(12) United States Patent
Sandford et al.

(10) Patent No.: US 9,399,113 B2
(45) Date of Patent: Jul. 26, 2016

(54) FLEXIBLE MEDICAL TUBING HAVING KINK RESISTANT PROPERTIES AND METHODS AND APPARATUS TO PRODUCE THE SAME

(71) Applicant: Fenwal, Inc., Lake Zurich, IL (US)

(72) Inventors: Craig Sandford, Buffalo Grove, IL (US); Dean R. Marshall, Ingleside, IL (US); Daniel R. Boggs, Libertyville, IL (US); Alvin Peralta-Faulkner, Santo Domingo (DO); Daryl Calhoun, Fox Lake, IL (US)

(73) Assignee: Fenwal, Inc., Lake Zurich, IL (US)

( * ) Notice: Subject to any disclaimer, the term of this patent is extended or adjusted under 35 U.S.C. 154(b) by 665 days.

(21) Appl. No.: 13/674,246

(22) Filed: Nov. 12, 2012

(65) Prior Publication Data
US 2013/0079753 A1   Mar. 28, 2013

Related U.S. Application Data

(63) Continuation-in-part of application No. PCT/US2011/051809, filed on Sep. 15, 2011.

(60) Provisional application No. 61/383,629, filed on Sep. 16, 2010.

(51) Int. Cl.
*A61M 25/00* (2006.01)
*A61M 39/08* (2006.01)
(Continued)

(52) U.S. Cl.
CPC ......... *A61M 25/005* (2013.01); *A61M 25/0009* (2013.01); *A61M 39/08* (2013.01);
(Continued)

(58) Field of Classification Search
CPC .... B29C 53/14; B29C 53/84; B29C 47/0023; B29C 47/0059; B29C 47/065; B29C 47/0866; B29C 47/0869; B29C 47/24; B29C 47/26; B29C 47/261; B29C 47/266; B29L 2031/753; B29L 2031/7542; A61M 25/0009; A61M 2025/0059
USPC ............... 264/171.26, 171.29, 173.16, 209.2, 264/312; 425/133.1, 404, 325
See application file for complete search history.

(56) References Cited

U.S. PATENT DOCUMENTS 4,717,326 A * 1/1988 Motonaga ........... B29C 47/0023
425/133.1
5,059,375 A   10/1991 Lindsay
(Continued)

FOREIGN PATENT DOCUMENTS

JP       2001190680 A *  7/2001

OTHER PUBLICATIONS

JP2001190680A JAP to ENG Machine Translation, translated Jun. 19, 2012.*

(Continued)

*Primary Examiner* — Alison L Hindenlang
*Assistant Examiner* — Lawrence D Hohenbrink, Jr.
(74) *Attorney, Agent, or Firm* — Cook Alex Ltd.

(57) ABSTRACT

A method is provided for making a tubing, which includes forming a generally tubular inner layer by flowing a first material through an extrusion assembly. At least one non-tubular segment is formed along the length of the tubing by flowing a second material through the extrusion assembly. A generally tubular outer layer coaxial with the inner layer is formed by flowing a third material through the extrusion assembly. The segment is positioned between the inner and outer layers and oriented non-tangentially with an interface between the inner and outer layers. The resulting tubing, which may be suitable for medical applications, may have kink-resistant properties.

10 Claims, 25 Drawing Sheets

(51) Int. Cl.
  *B29C 47/00* (2006.01)
  *B29C 47/06* (2006.01)
  *B29C 47/24* (2006.01)
  *B29L 23/00* (2006.01)
  *B29L 31/00* (2006.01)

(52) U.S. Cl.
  CPC .......... *B29C47/0023* (2013.01); *B29C 47/064* (2013.01); *B29C 47/24* (2013.01); *A61M 25/0012* (2013.01); *A61M 2025/0059* (2013.01); *B29L 2023/007* (2013.01); *B29L 2031/7542* (2013.01); *B29L 2031/7732* (2013.01)

(56) References Cited

U.S. PATENT DOCUMENTS

| | | | | |
|---|---|---|---|---|
| 5,928,744 A | * | 7/1999 | Heilmann | A61L 29/14 138/137 |
| 6,129,876 A | * | 10/2000 | Qin | A61M 39/08 264/209.5 |
| 2002/0076464 A1 | | 6/2002 | Guillemette et al. | |
| 2003/0077347 A1 | * | 4/2003 | Miebach | B29C 47/0007 425/133.1 |
| 2003/0165647 A1 | | 9/2003 | Kaneko et al. | |
| 2004/0236310 A1 | | 11/2004 | Chin et al. | |
| 2005/0260408 A1 | | 11/2005 | Anand et al. | |
| 2006/0189896 A1 | | 8/2006 | Davis et al. | |
| 2007/0276354 A1 | * | 11/2007 | Osborne | A61M 25/0012 604/527 |
| 2008/0015547 A1 | * | 1/2008 | Beisel | A61M 25/001 604/523 |

OTHER PUBLICATIONS

Extended European Search Report and Search Opinion for European Patent Appln. No. 11825963.9, dated Dec. 14, 2014.

International Search Report and Written Opinion for PCT application No. PCT/US2011/051809, dated Apr. 30, 2012.

International Preliminary Report on Patentability for PCT application No. PCT/US2011/051809, dated Feb. 7, 2013.

* cited by examiner

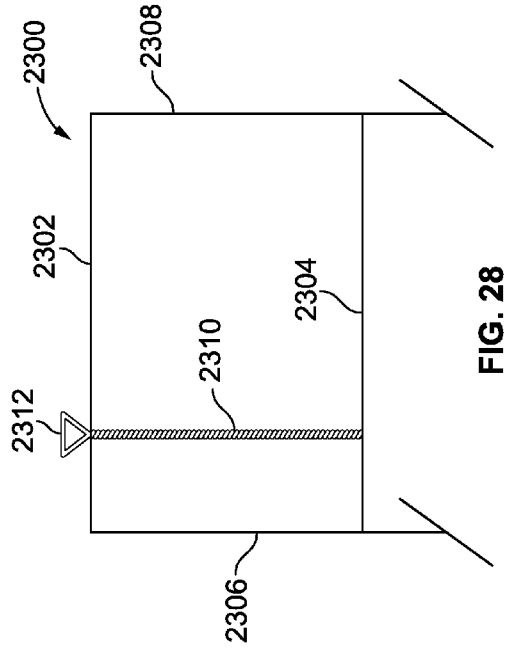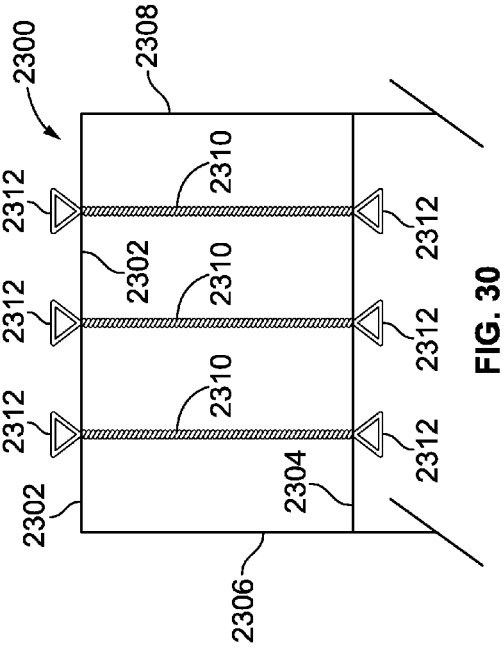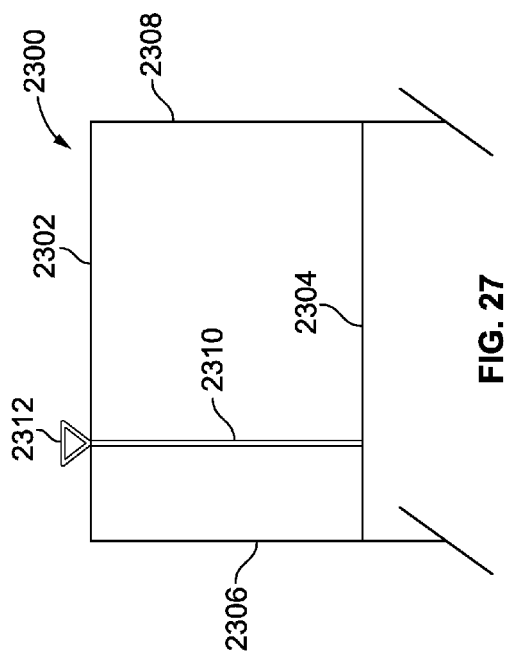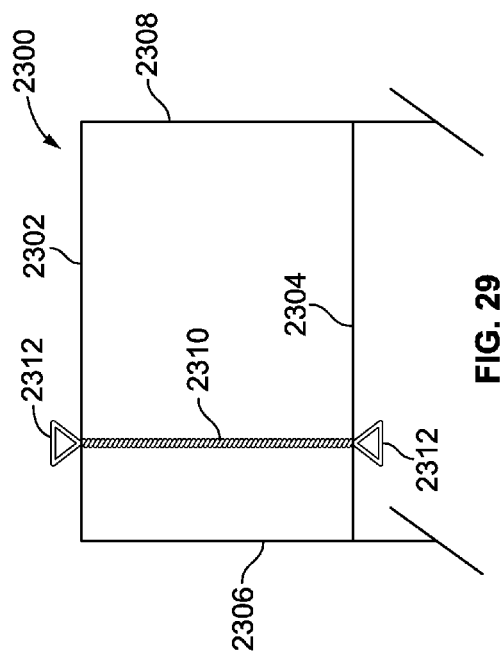

FLEXIBLE MEDICAL TUBING HAVING KINK RESISTANT PROPERTIES AND METHODS AND APPARATUS TO PRODUCE THE SAME

CROSS-REFERENCE TO RELATED PATENT APPLICATIONS

This application is a continuation-in part of PCT Patent Application No. PCT/US2011/051809, filed Sep. 15, 2011, which claims the benefit of U.S. Provisional Application No. 61/383,629, titled "Tubing Having Kink Resistant Properties and Methods and Apparatuses to Produce The Same," filed Sep. 16, 2010, both of which are incorporated herein by reference in their entirety.

BACKGROUND

1. Field of the Disclosure

This application relates to flexible medical tubing and, more specifically, to medical flexible tubing having kink resistant properties and methods and apparatuses to produce the same.

2. Description of Related Art

Tubing, for example plastic or polymer tubing, may be used in many medical applications. For example, medical tubing may be used to carry therapeutic fluids (e.g., medicines, saline, nutrient fluids, etc.) or to carry biological fluids (e.g., blood, urine, etc.). Medical tubing may become occluded through the formation of kinks limiting the ability of the tube to effectively carry fluid.

SUMMARY

There are several aspects of the present subject matter, which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a method is provided for making a tubing. A generally tubular inner layer is formed by flowing a first material through an extrusion assembly. At least one non-tubular segment is formed along the length of the tubing by flowing a second material through the extrusion assembly. A generally tubular outer layer coaxial with the inner layer is formed by flowing a third material through the extrusion assembly. The segment is positioned between the inner and outer layers and oriented non-tangentially with an interface between the inner and outer layers.

BRIEF DESCRIPTION OF THE DRAWINGS

FIG. 27 is a perspective view of a frame suitable for post-formation addition of a helical structure to a tubing.

FIG. 28 is a perspective view of the frame of FIG. 27, with a tubing twisted and partially secured to the frame.

FIG. 29 is a perspective view of the frame of FIG. 27, with a tubing twisted and secured to two locations of the frame.

FIG. 30 is a perspective view of the frame of FIG. 27, with a plurality of twisted tubings secured therein.

DESCRIPTION OF THE ILLUSTRATED EMBODIMENTS

The embodiments disclosed herein are for the purpose of providing the required description of the present subject matter. They are only exemplary, and may be embodied in various forms. Therefore, specific details disclosed herein are not to be interpreted as limiting the subject matter as defined in the accompanying claims.

The examples described herein relate to example apparatus to produce tubing having kink resistant properties. Additionally, the examples described herein relate to tubing having kink resistant properties. In some examples, tubing having kink resistant properties may be produced using a non-rotating die design. In some examples, tubing having kink resistant properties may be produced using a rotating and/or partially rotating die design. In some examples, tubing having kink resistant properties may be produced using one or more rotating features external to the die.

In some examples, the apparatus includes an extrusion assembly that induces generally helical and/or generally spiral fluid flow enabling tubing to be produced having generally helical and/or generally spiral non-homogeneity characteristics. In some examples, the apparatus includes a fixture that emits light that cross-links and/or chemically modifies tubing after extrusion to enable tubing to be produced having helical and/or spiral non-homogeneity characteristics. In some examples, the apparatus includes a plurality of helical rollers that rotate tubing and/or relative to tubing after it exits the extrusion die to produce tubing having helical and/or spiral non-homogeneity characteristics.

Figure 1:
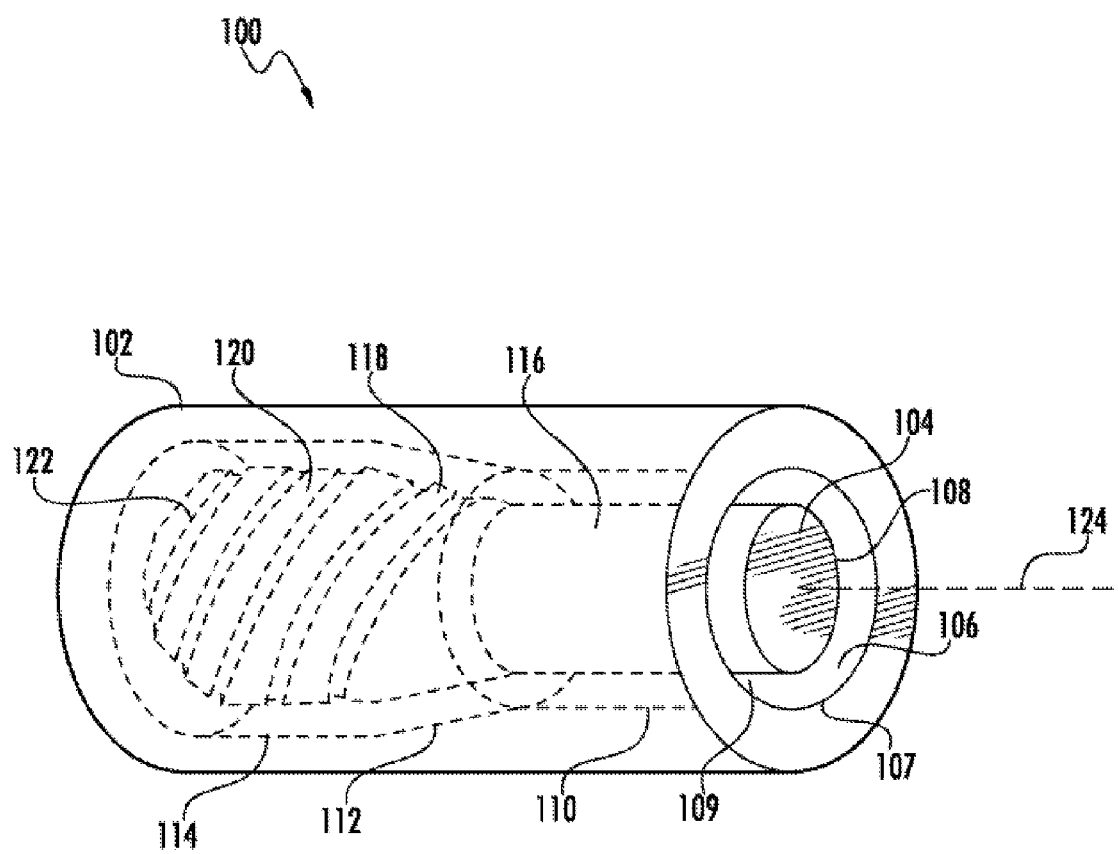
FIG. 1 depicts an example extrusion assembly used to produce tubing having non-homogeneity characteristics.

FIG. 1 depicts an example extrusion assembly 100 that induces a helical flow in fluid (e.g., polymers) flowing therethrough by inducing a helical high shear field. Inducing helical fluid flow enables tubes to be extruded having helical non-homogeneity characteristics. This helical non-homogeneity enables the tubing produced to have kink resistant properties. The example extrusion assembly 100 includes an example extrusion bushing 102 and an example extrusion pin 104. The bushing 102 and the pin 104 are at least partially separated by a flow channel 106 defined by an interior surface 107 of the bushing 102 and an exterior surface 108 of the pin 104. In some examples, the interior surface 107 and/or the exterior surface 108 may be at least partially corrugated. In some examples, the exterior surface 108 may be configured to produce tubing having an aperture having a particular cross-section such as, for example, a star shaped cross-section, a triangular cross-section, a circular cross-section, etc. The corrugation and/or the cross-section of the exterior surface 108 may enable tubing produced to have kink resistant properties.

The bushing 102 defines a channel 109 having a first channel portion 110, a tapered channel portion 112 and a second channel portion 114. The pin 104 includes a first pin portion 116 positioned at least partially within the first channel portion 110, a tapered pin portion 118 positioned at least partially within the tapered channel portion 112 and a second pin portion 120 positioned at least partially within the second channel portion 114.

In this example, to induce a spiral high shear field and, thus, a helical flow pattern in the fluid (e.g., polymers) flowing through the flow channel 106, the tapered pin portion 118 and/or the second pin portion 120 define and/or include a plurality of helical grooves, protrusions and/or flanges 122. The grooves 122 may be positioned at an angle (e.g., a non-parallel angle, a thirty degree angle, a thirty five degree angle, etc.) relative to a longitudinal axis 124 of the extrusion assembly 100.

In practice, as the fluid flows past the grooves 122, a helical flow pattern is induced in the fluid flow by the grooves 122. The helical flow pattern enables tubes (e.g., medical tubes) to be produced having non-homogeneity (e.g., helical non-homogeneity) therein. While the tapered pin portion 118 and/or the second pin portion 120 are depicted as defining the grooves 122, any other surface structure, texture, etc. may be included and/or defined to induce a desired flow pattern within the flow channel 106 and/or to enable tube(s) to be produced having helical non-homogeneity therein.

In an exemplary embodiment, the second channel portion 114 of bushing 102 may include and/or define grooves, protrusions and/or flanges to induce a helical flow pattern in the fluid flowing through the flow channel 106 in addition to or in place of groove 122 of pin 104.

Figure 2:
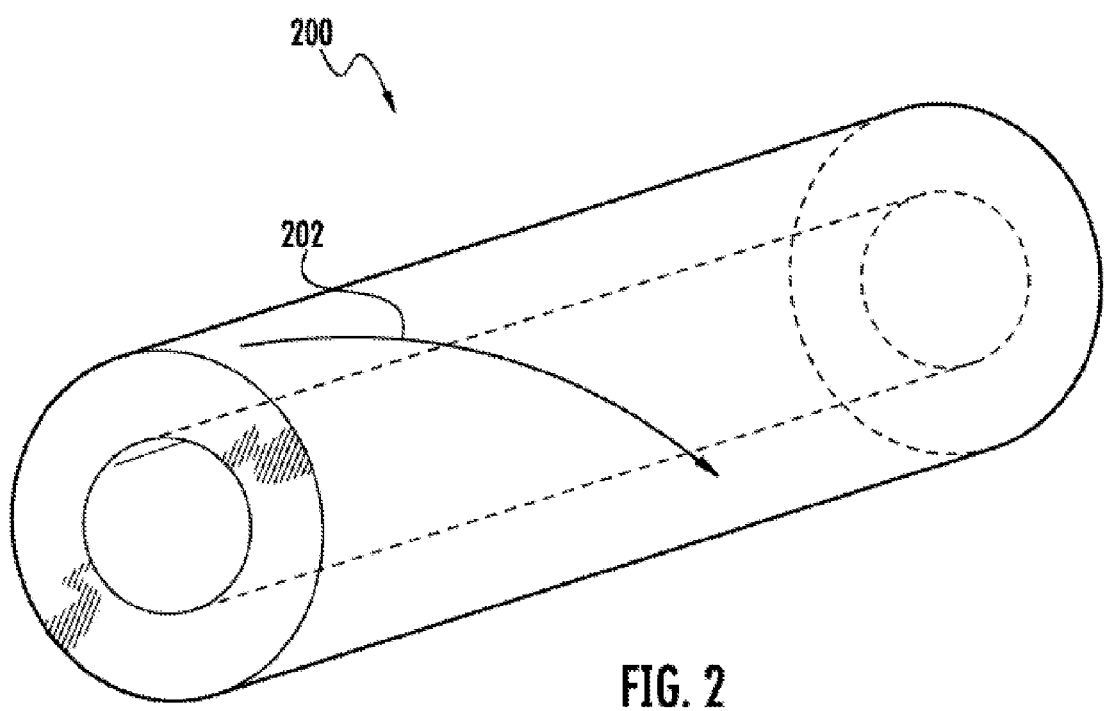
FIG. 2 depicts an example tube that can be produced using the examples described herein.

FIG. 2 depicts an example tube 200 having a generally helical structure, shown as helical pattern 202, therein that enables the tube 200 to be relatively kink resistant. In some examples, the helical pattern 202 may include portions (e.g., coils) that are evenly spaced from one another. In some examples, the helical pattern 202 may include portions (e.g., coils) that are unevenly spaced from one another. In some examples, the helical pattern 202 may have the same or a similar pitch along the length of tube 200. In some examples, the helical pattern 202 may have a varying or different pitch along the length of tube 200. In some examples, an optimum pitch may have a spacing lower limit (e.g., spacing between coils) and a spacing upper limit (e.g., spacing between coils) to enable tubing produced to have particular kink resistant properties. For example, the spacing lower limit may be relatively small and/or less than the diameter of the tubing and/or a stripe or rod of material positioned therein and the spacing upper limit may be relatively large and/or greater than the diameter of the tubing and/or a stripe or rod of material positioned therein.

The helical pattern 202 may be produced by the orientation of polymer chains in the tube 200, for example. In other examples, helical pattern 202 may represent a helically positioned section of a material that is different (e.g., different material type, composition or polymer, that has a different flexibility, rigidity, hardness or durometer, etc.) than the material that forms the body of tube 200. In one such example, tube 200 may include three or more helical patterns 202 formed of material having a greater durometer than the material that forms the body of tube 200. The example tube 200 may be produced using any of the examples described herein such as, for example, the example extrusion assembly 100.

Figure 3:
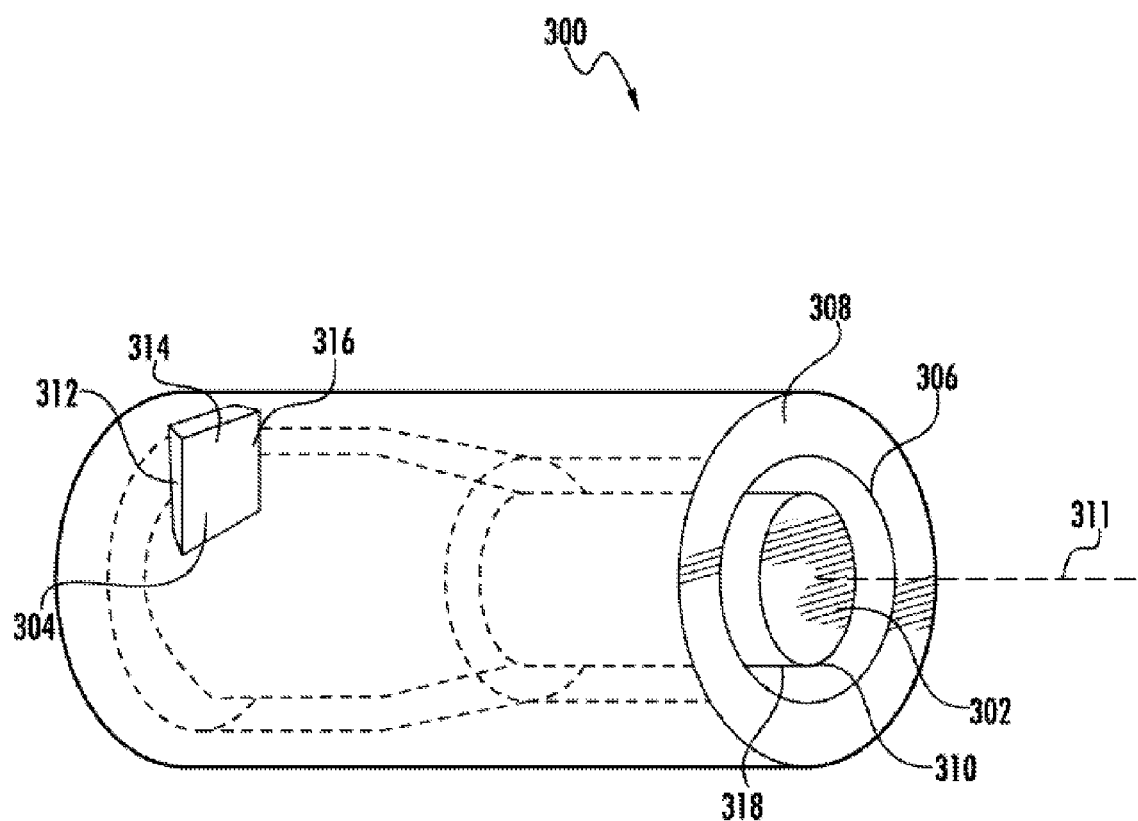
FIG. 3 depicts another example extrusion assembly used to produce tubing having non-homogeneity characteristics.

FIG. 3 depicts an example extrusion assembly 300 that induces a helical flow in fluid (e.g., polymers) flowing therethrough to enable tubes to be extruded having helical non-homogeneity characteristics. This helical non-homogeneity enables the tubing produced to have kink resistant properties. In contrast to the extrusion assembly 100 described above, an extrusion pin 302 of the extrusion assembly 300 may not be provided with the grooves 122, but instead, the extrusion assembly 300 includes an example flow control member or arm 304 (e.g., an angled wall, a baffle, a vane, a spider leg, a fin, etc.). The flow control member 304 is coupled between an interior surface 306 of an example extrusion bushing 308 and an exterior surface 310 of the pin 302. In some examples, the flow control member 304 is positioned at an angle (e.g., a non-parallel angle, a thirty degree angle, a thirty-five degree angle, a forty degree angle, etc.) relative to a longitudinal axis 311 of the extrusion assembly 300.

While the extrusion assembly 300 is depicted as having one flow control member 304, the extrusion assembly 300 may have any other number of flow control members (e.g., 2, 3, 4, etc.). If the extrusion assembly 300 includes more than one flow control member 304, the flow control members 304 may be similar or different from one another, for example. If the extrusion assembly 300 includes more than one flow control member 304, the flow control members 304 may be positioned around a circumference of the exterior surface 310 of the pin, for example. Additionally or alternatively, if the extrusion assembly 300 includes more than one flow control member 304, the flow control members 304 may be positioned (e.g., circumferentially positioned and/or axially positioned) along the longitudinal axis 311 of the extrusion assembly 300 between the interior surface 306 and the exterior surface 310, for example.

The flow control member 304 may include a first side 312, a middle portion 314 and a second side 316. In some examples, the first side 312, the middle portion 314 and the second side 316 have a similar thickness. In some examples, the first side 312 has a thickness different than a thickness of the middle portion 314 and/or the second side 316. In some examples, the middle portion 314 has a thickness different than a thickness of the first side 312 and/or the second side 316. In some examples, the second side 316 has a thickness different than a thickness of the first side 312 and/or the middle portion 314. Additionally or alternatively, any of the first side 312, the middle portion 314 and/or the second side 316 may have a substantially consistent thickness or a varying thickness, for example. For example, a portion of the flow control member 304 coupled to the exterior surface 310 may have a different thickness than a portion of the flow control member 304 coupled to the interior surface 306.

In some examples, materials such as fibers and/or fibrous inclusions may be introduced into, for example, polymer pellets used to produce tubing prior to extrusion and/or processing. Such fibers and/or fibrous inclusions enable tubing to be produced having fibers therein. The fibers may be nylon, polyester or any other material that does not melt during processing (e.g., PVC processing). In some examples, the fibers and/or fibrous inclusions may form in the polymer after extrusion of the tubing. In some examples, the fibers may have an index of refraction that is similar to the bulk material (e.g., the first polymer) of the tubing wall.

In practice, as the fluid flows through the flow channel 318 past the flow control member 304, a helical flow pattern is induced in the fluid flow by the flow control member 304. The helical flow pattern enables tubing (e.g., medical tubes) to be produced having non-homogeneity (e.g., helical non-homogeneity) characteristics.

Figure 4:
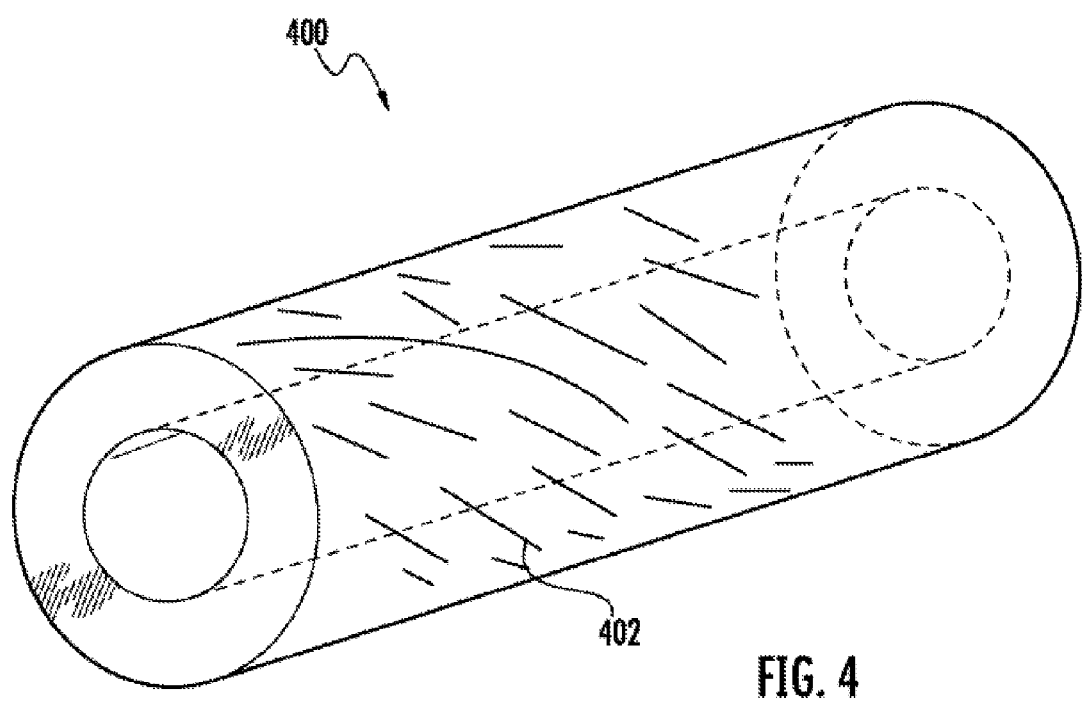
FIG. 4 depicts an example tube that can be produced using the examples described herein.

FIG. 4 depicts an example tube 400 having a helical structure, shown as helically oriented or aligned fibers and/or fibrous inclusions 402. The helical pattern and/or the fibers 402 enable the tube 400 to be relatively kink resistant. In some examples, the fibers may be added to the polymer pellets prior to extrusion and/or processing and/or may form in the tubing after extrusion. The example tube 400 may be produced using any of the examples described herein such as, for example, the example extrusion assembly 300.

Figure 5:
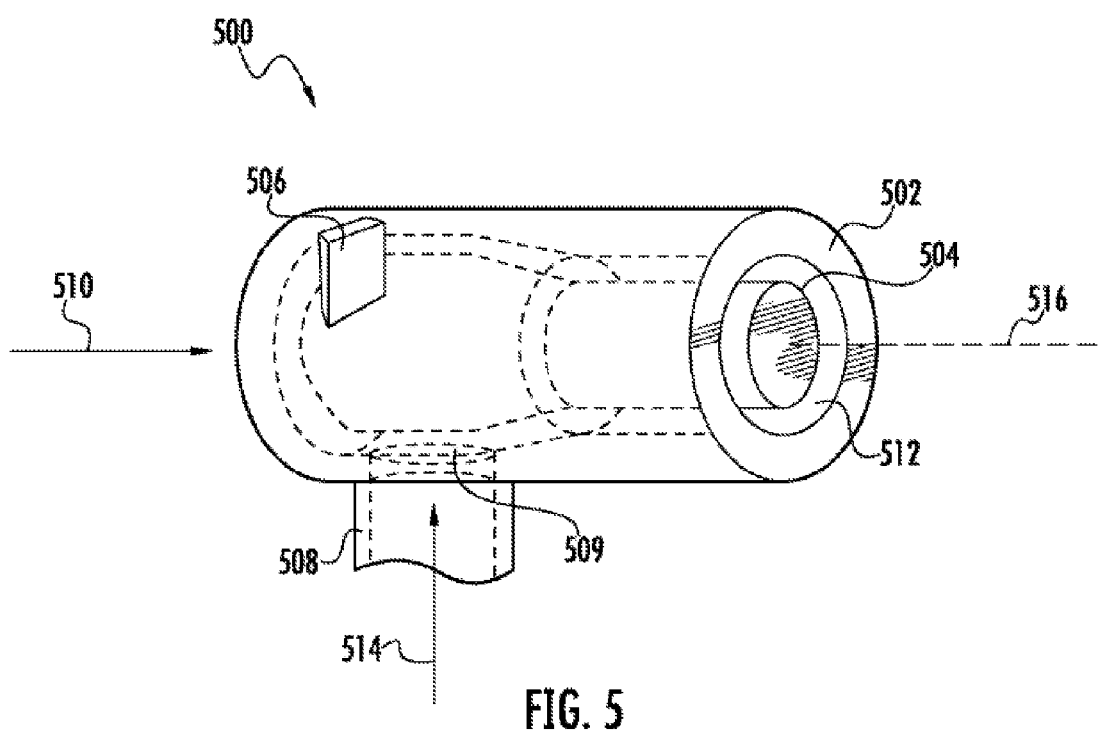
FIG. 5 depicts another example extrusion assembly used to produce tubing having non-homogeneity characteristics.

FIG. 5 depicts an example extrusion assembly 500 that induces a helical flow in fluid (e.g., polymers) flowing therethrough to co-extrude tubes having helical non-homogeneity characteristics. This helical non-homogeneity enables the tubing produced to have kink resistant properties. The example extrusion assembly 500 includes an example extrusion bushing 502, an example extrusion pin 504, an example flow control member 506 and a side port 508. The example flow control member 506 may be similar to the example flow control member 304 of FIG. 3. The side port 508 may be differently positioned (e.g., different angles and/or positions relative to the bushing 502) to produce different tubes. For example, an opening 509 of the side port 508 may be positioned adjacent an exterior surface of the pin 504. The opening 509 of the side port 508 may be positioned adjacent an interior surface of the bushing 502, for example. The opening 509 of the side port 508 may be positioned between the interior surface of the bushing 502 and the exterior surface of the pin 504, for example. The side port 508 may be positioned at any distance relative to an end of the extrusion assembly 500 to induce spiral flow and/or to ensure a relatively consistent fluid flow from the extrusion assembly 500, for example.

In practice, in some examples, a first polymer or material (e.g., bulk material, bulk extrudate, plasticized PVC, Shore A 77, a first durometer) may flow in a direction generally represented by arrow 510 into a flow channel 512 between the bushing 502 and the pin 504. In some examples, a second polymer (e.g., plasticized PVC, Shore A 85, a second durometer) may flow in a direction generally represented by arrow 514 into the flow channel 512. The first polymer may be similar or different than the second polymer and may be compatible with the second polymer. For example, the first polymer may have a first modulus and the second polymer may have a second modulus different from the first modulus. In some examples, the second polymer has a higher modulus than the first polymer. The first polymer may flow into the flow channel 512 at a first flow rate and the second polymer may flow into the flow channel 512 at a second flow rate. The first flow rate may be similar or different than the second flow rate. For example, the volume of flow of the second polymer may be approximately ten percent of the volume of flow of the first polymer.

As the first polymer flows through the flow channel 512 past the flow control member 506, a helical flow pattern is induced in the fluid flow by the flow control member 506. As the second polymer enters the flow channel 512, the second polymer may create a helical ribbon on and/or in the tube being produced. In examples in which the opening 509 is positioned adjacent the interior surface of the bushing, the addition of the second polymer enables tubing to be produced having a helical ribbon on an exterior surface of the tube. In examples in which the opening 509 is positioned between the interior surface of the bushing 502 and the exterior surface of the pin 504, the tubing produced may have a helical ribbon or rib imbedded in the tubing wall. In examples in which the side port 508 is positioned at an angle (e.g., a non-perpendicular angle, a perpendicular angle) relative to a longitudinal axis 516 of the extrusion assembly 500, the second polymers entering the flow channel 512 may further induce a helical flow pattern in the fluid flowing in the flow channel 512. As with the other examples described herein, the tubing produced using the example extrusion assembly 500 include non-homogeneity (e.g., helical non-homogeneity) therein.

Figure 6:
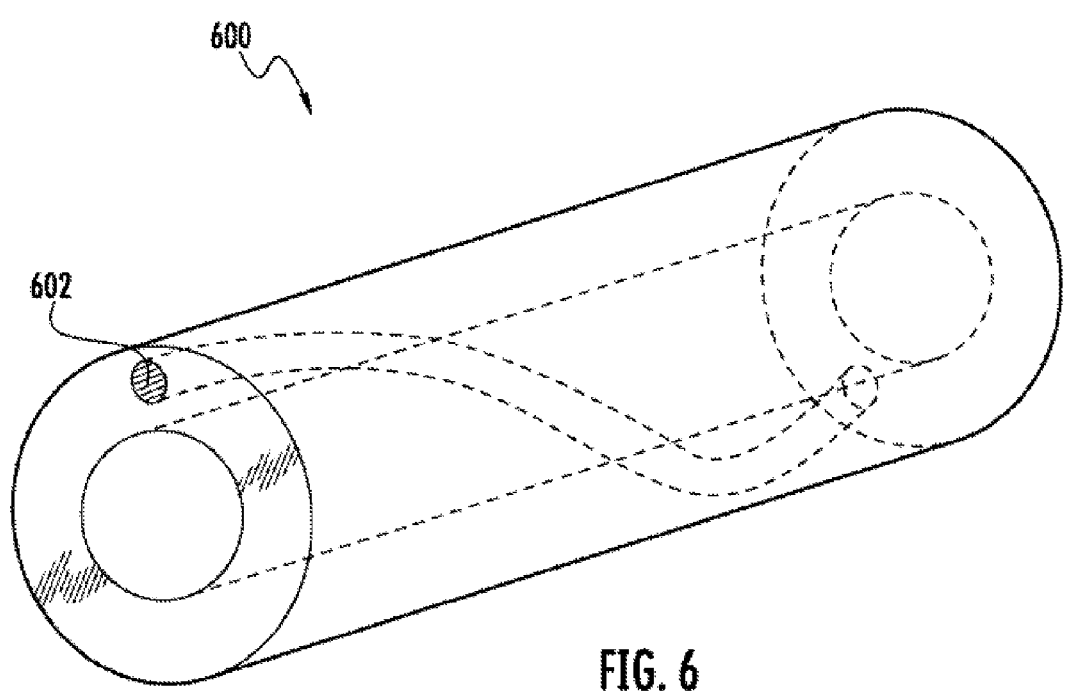
FIG. 6 depicts an example tube that can be produced using the examples described herein.

FIG. 6 depicts an example tube 600 that can be produced using the examples described herein such as using the example extrusion assembly 500. The tube 600 includes a helical structure, shown as helical co-extruded section, portion or rod 602, positioned therein. The rod 602 may be a different modulus (e.g., a higher modulus) than the remainder (e.g., bulk) of the tube 600. The rod 602 enables the tube 600 to be relatively kink resistant. In some examples, the rod 602 may include portions (e.g., coils) that are evenly spaced from one another and/or the rod 602 may include portions that are evenly spaced from a longitudinal axis of the tube 600. In some examples, the rod 602 may include portions (e.g., coils) that are unevenly spaced from one another and/or the rod 602 may include portions that are unevenly spaced from a longitudinal axis of the tube 600. In some examples, the rod 602 may have a minimum volume and a maximum volume. For example, the minimum volume may be approximately one percent of a tube 100 wall volume and the maximum volume may be approximately fifty percent of the tube 100 wall volume; however, different percentages (e.g., 2, 3, 4, etc.) may be used for the minimum volume and different percentages (e.g., 48, 49, 50, 51, etc.) may be used for the maximum volume. In one example, tube 600 may include more than one rod 602, and in one specific example, tube 600 includes three or more rods 602.

Figure 7:
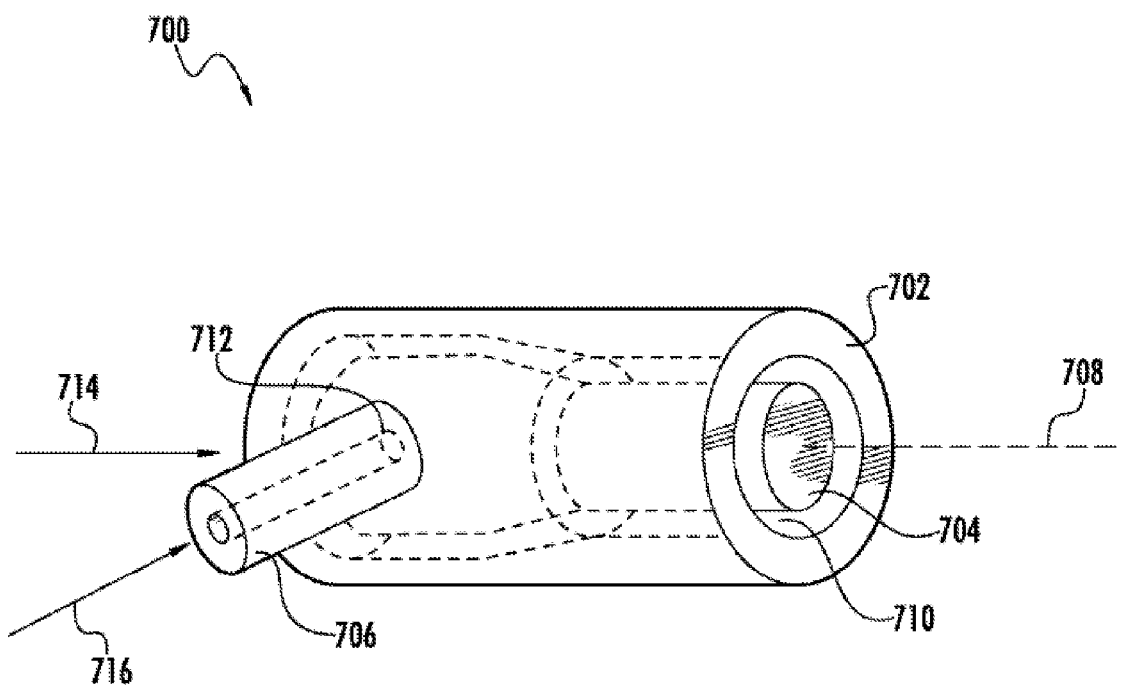
FIG. 7 depicts another example extrusion assembly used to produce tubing having non-homogeneity characteristics.

FIG. 7 depicts an example extrusion assembly 700 that induces helical flow in fluid flowing therethrough to co-extrude tubes having helical non-homogeneity characteristics. This helical non-homogeneity enables the tubing produced to have kink resistant properties. The example extrusion assembly 700 includes an example extrusion bushing 702, an example extrusion pin 704 and an example angled side port 706. The side port 706 may be positioned at any suitable angle (e.g., a sixty degree angle, a seventy degree angle, an eighty degree angle, a ninety degree angle, etc.) relative to a longitudinal axis 708 of the example extrusion assembly 700. The angle of the side port 706 relative to a flow channel 710 between the bushing 702 and the pin 704 enables fluid flowing though the side port 706 to induce a helical flow in fluid flowing through the flow channel 710. The side port 706 may be differently positioned to produce different tubes. For example, an opening 712 of the side port 706 may be positioned adjacent an exterior surface of the pin 704. The opening 712 of the side port 706 may be positioned adjacent an interior surface of the bushing 502, for example. The opening 712 of the side port 706 may be positioned between the interior surface of the bushing 702 and the exterior surface of the pin 704, for example.

In practice, first polymers (e.g., bulk material, bulk extrudate) entering the flow channel 710 flow in a direction generally represented by arrow 714 and second polymers (e.g., stiffer PVC) entering the flow channel 710 flow in the direction generally represented by arrow 716. The angle at which the side port 706 is positioned relative to the flow channel 710 induces a helical flow pattern in the fluid flow when the second polymers enter the flow channel 710. Additionally, as the second polymers enter the flow channel 710, the second polymers may create a helical ribbon on and/or in the tube being produced. In examples in which the opening 712 is positioned adjacent the interior surface of the bushing 702, the addition of the second polymers enables a tube to be produced having a helical ribbon on the exterior surface of the tube. As with the other examples described herein, the tubes produced using the example extrusion assembly 700 include non-homogeneity (e.g., helical non-homogeneity) therein.

Figure 8:
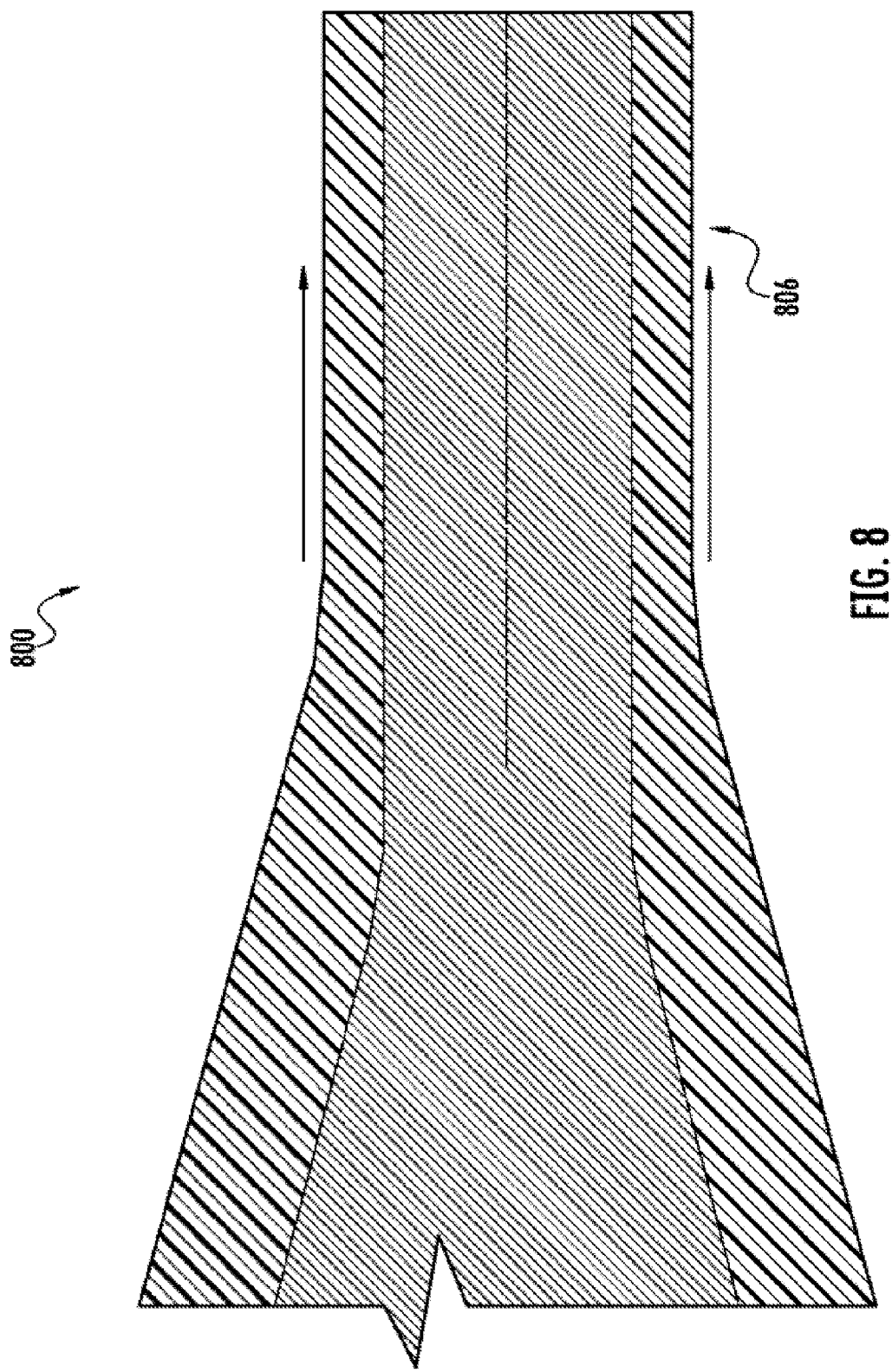
FIG. 8 depicts a side view of an example of fluid flowing through the example extrusion assembly of FIG. 7.
Figure 9:
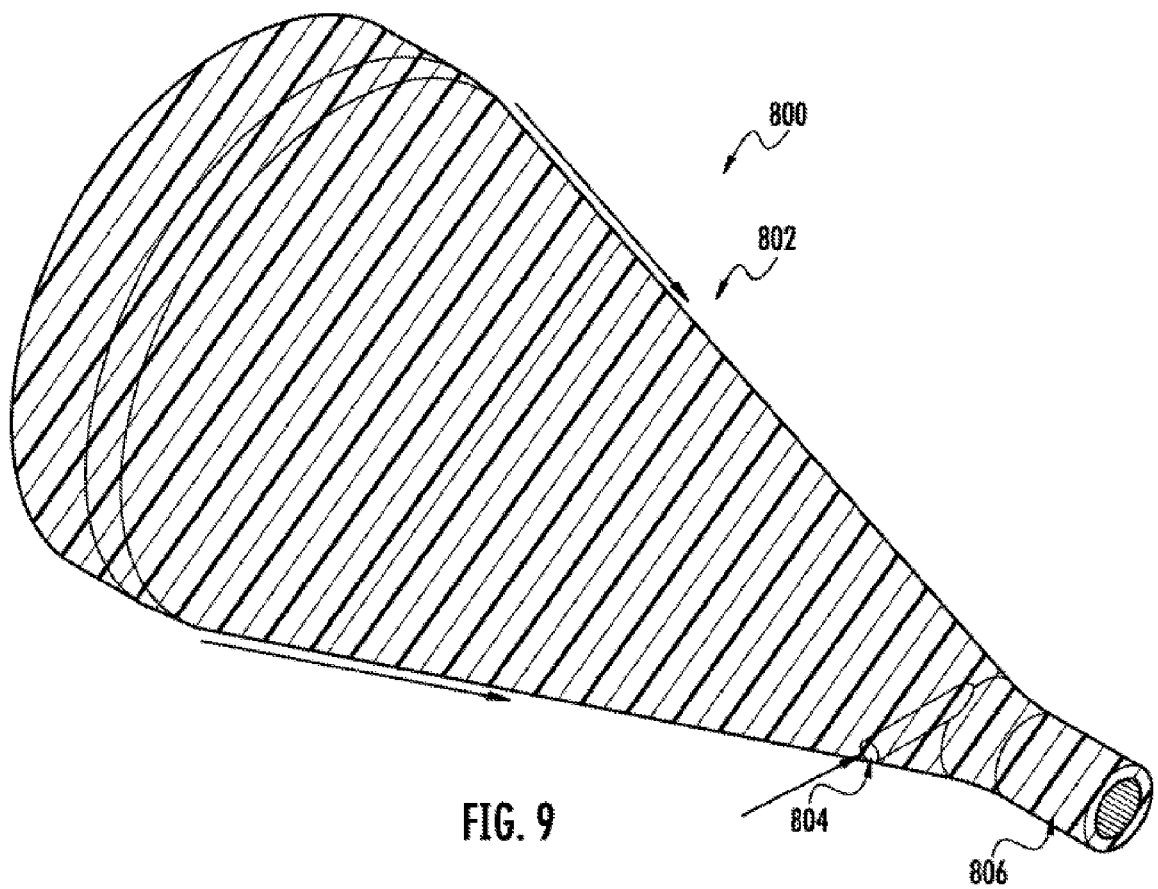
FIG. 9 depicts a perspective view of the fluid flow of FIG. 8.
Figure 10:
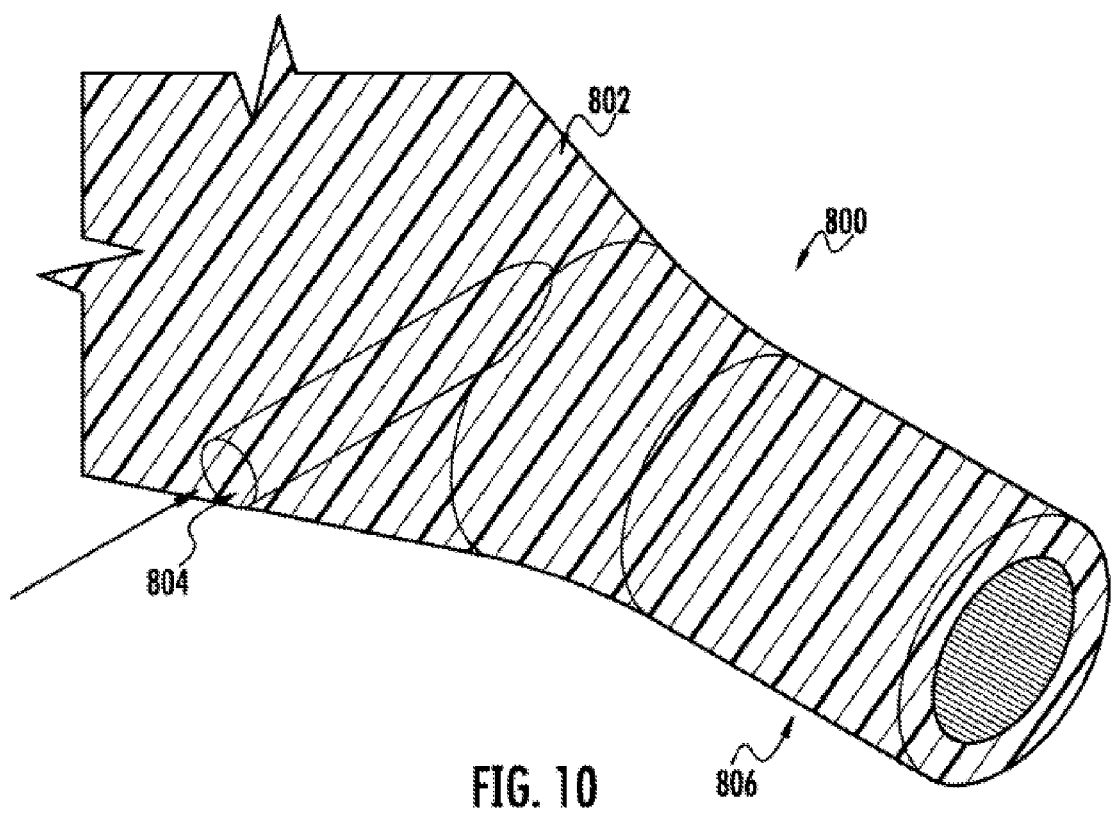
FIG. 10 depicts an enlarged view of a portion of the fluid flow shown in FIG. 9.

FIGS. 8-10 depict the flow path 800 of the fluid flowing through the example extrusion assembly 700. Reference number 802 represents the flow of first polymers, reference number 804 represents the flow of second polymers and reference number 806 represents the flow of first and second polymers.

Figure 11:
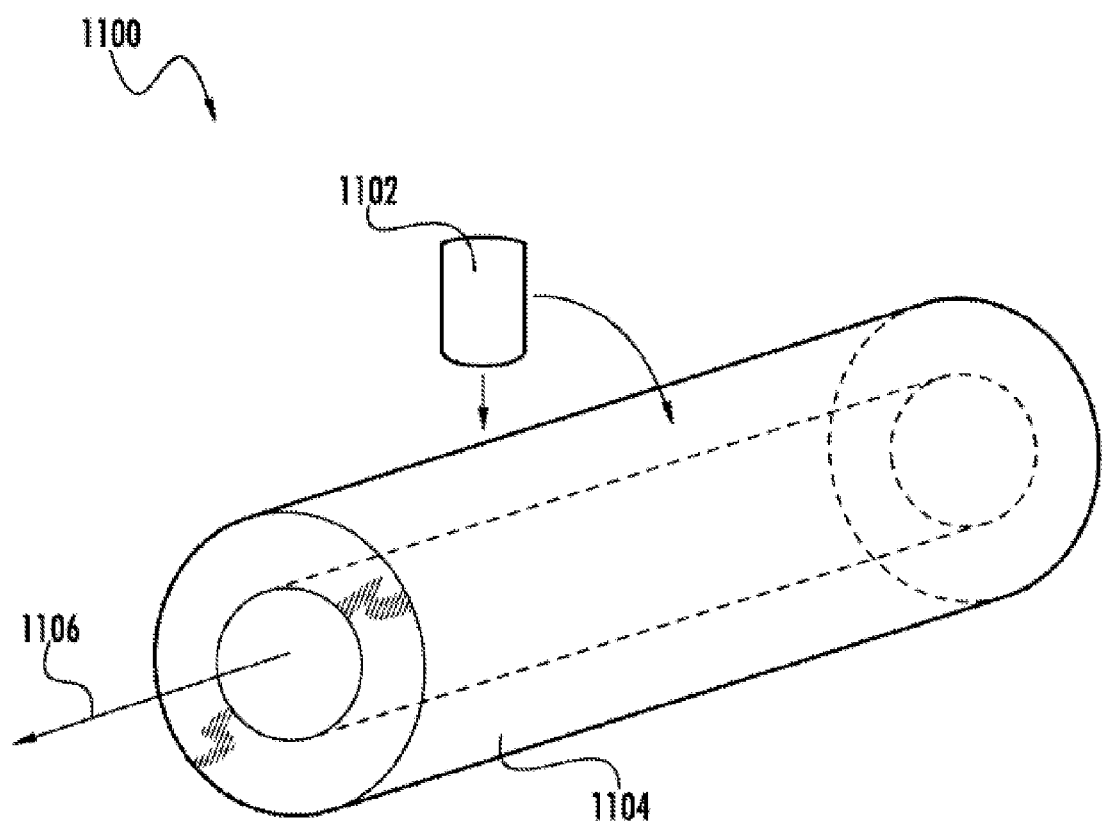
FIG. 11 depicts an example cross-linking apparatus used to induce a generally helical geometry in tubing after extrusion.

FIG. 11 depicts an example apparatus 1100 that enables helical orientation cross-linking and/or chemical modification to be obtained in tubing (e.g., medical tubes) being produced using, for example, the example extrusion assemblies described herein. The example apparatus 1100 includes a cross-linking beam or fixture 1102 that may rotate around a tube 1104 being extruded in a direction (e.g., a longitudinal direction) generally represented by arrow 1106. In some examples, the fixture 1102 may define an aperture (not shown) through which the tube 1104 passes. The fixture 1102 may emit ionizing radiation, ultraviolet radiation, etc., as the fixture 1102 is rotated about the tube 1104 as the tube 1104 is being extruded, for example. Rotating the fixture 1102 about the tube 1104 as the tube 1104 is being extruded cross-links polymers in the tube 1104 in a generally helical orientation. The example apparatus 1100 may be utilized in connection with any of the extrusion assemblies described herein to further induce helical non-homogeneity or may be used on its own to produce tubes having helical non-homogeneity, for example.

Figure 12:
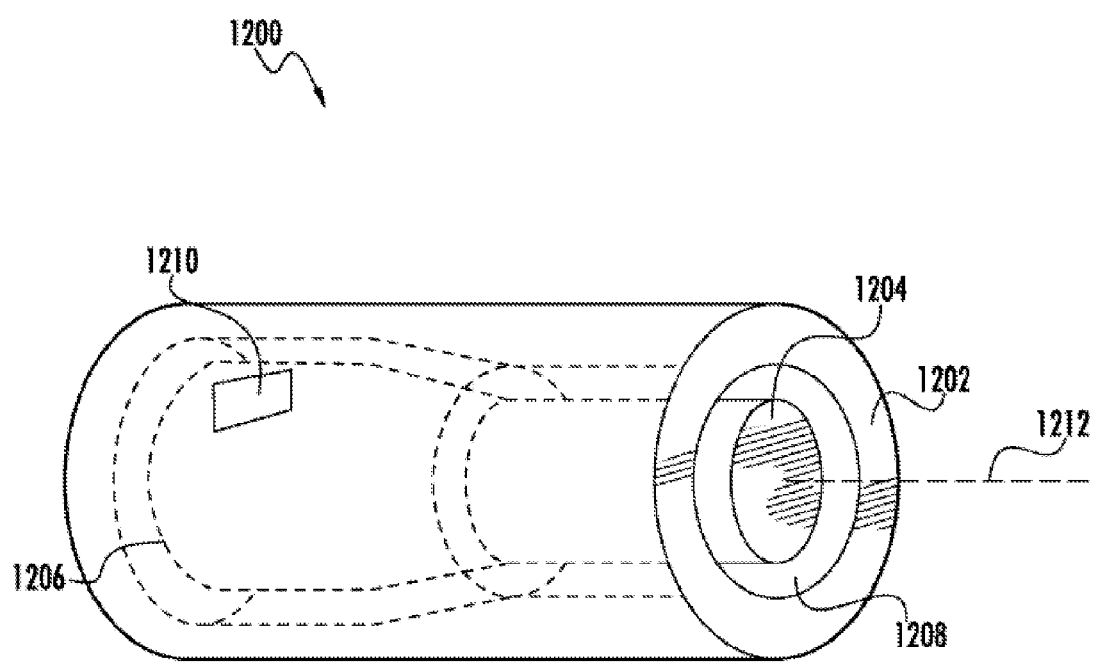
FIG. 12 depicts another example extrusion assembly used to produce tubing having non-homogeneity characteristics.

FIG. 12 depicts an example extrusion assembly 1200 that induces a spiral high shear field and, thus, a helical flow in fluid flowing therethrough to enable tubes to be extruded having helical non-homogeneity characteristics. The example extrusion assembly 1200 includes an example extrusion bushing or rotating extrusion bushing 1202 and an example extrusion pin or rotating extrusion pin 1204. In contrast to the examples described above, the extrusion pin 1204 may be coupled to a bearing mount 1206 to enable the extrusion pin 1204 to rotate (e.g., rotate freely) as fluid flows through a flow channel 1208 between the bushing 1202 and the pin 1204. In practice, a helical flow pattern is induced in fluid flowing through the flow channel 1208 by a flow control member or fin 1210. The helical fluid flow may in turn provide the rotational driving force to rotate the extrusion pin 1204, for example. The flow control member 1210 may include different geometries to provide an angled surface to induce helical fluid flow. The flow control member 1210 may be positioned at an angle (e.g., a non-parallel angle) relative to a longitudinal axis 1212 of the extrusion assembly 1200.

Figure 13:
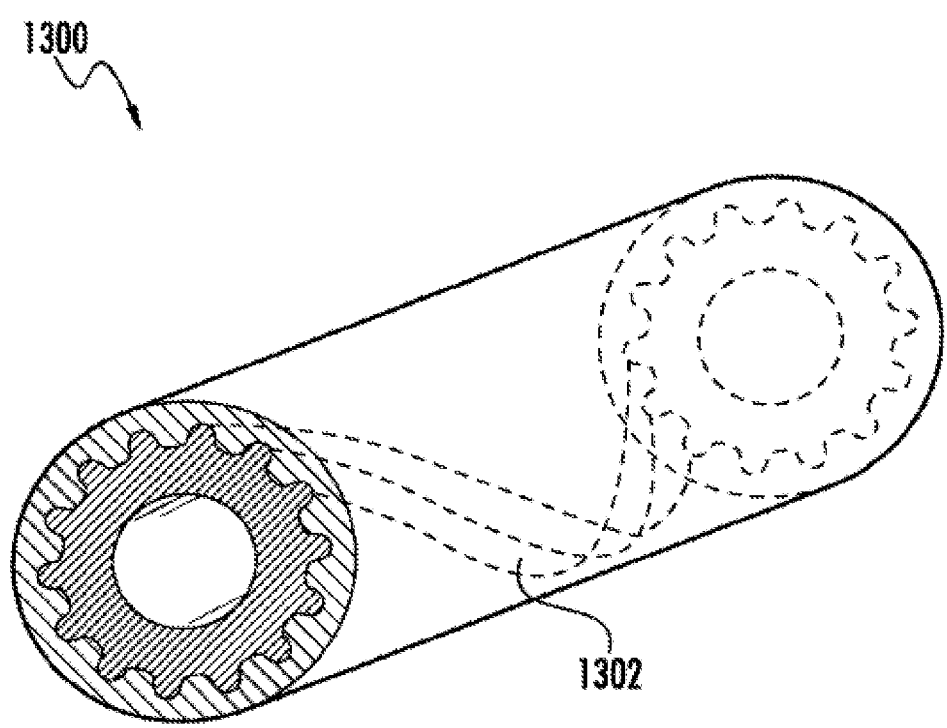
FIG. 13 depicts an example tube having non-homogeneity characteristics.

FIG. 13 depicts an example tube 1300 having a helical structure, shown as helical co-extruded profile (e.g., a co-extruded gear profile). In some examples, the tube 1300 includes a helical and/or rotation of a gear profile 1302 positioned within the tube 1300. The helical gear profile 1302 enables the tube 1300 to be relatively kink resistant. In some examples, an extrusion assembly used to produce the example tube 1300 may be similar to the extrusion assemblies 100, 300 and/or 700 configured for co-extrusion. In other examples, the extrusion assembly used to produce the example tube 1300 may induce helical flow in the fluid flowing therethrough.

Figure 14:
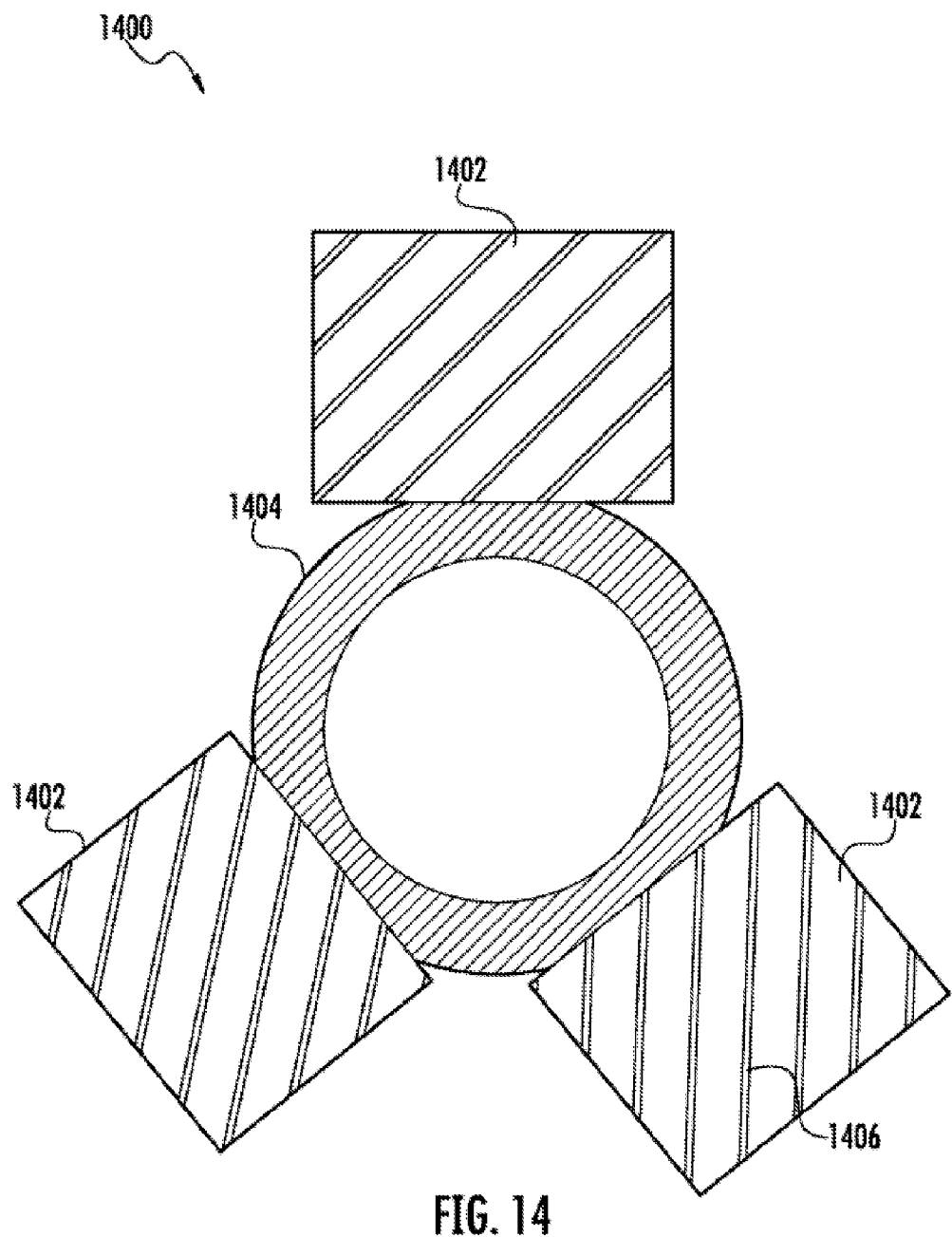
FIG. 14 depicts an example apparatus used to induce a generally helical geometry in tubing after extrusion.

FIG. 14 depicts an example apparatus 1400 that enables helical orientation to be obtained in tubing (e.g., medical tubes) being produced using, for example, the example extrusion assemblies described herein. The example apparatus 1400 includes a plurality of helical rollers 1402 external to the extrusion die and positioned about tubing 1404 being extruded. In other examples, the example apparatus 1400 may include a plurality of conical or spiral rollers. In some examples, the apparatus 1400 may be positioned in a tubing water quench tank.

The plurality of rollers 1402 defines and/or includes a plurality of grooves and/or surface structures 1406 that may induce helical non-homogeneity in tubing and/or induce rotation of the tubing 1404 as the tubing is being pulled through the rollers 1402 by, for example, downstream take-up. In some examples, the plurality of rollers 1402 may be free spinning on bearings.

In practice, as the tubing 1404 exits an extrusion die prior to quenching, helical orientation is induced in the molten portion of the tubing 1404 by the rollers 1402 rotating the tubing 1404. While the example apparatus 1400 includes three rollers 1402, any other number of rollers (e.g., 1, 2, 3, etc.) may be used instead to induce helical non-homogeneity and/or induce rotation. The example apparatus 1400 may be utilized in connection with any of the extrusion assemblies described herein to further induce helical non-homogeneity or may be used on its own to produce tubes having helical non-homogeneity, for example.

Figure 15:
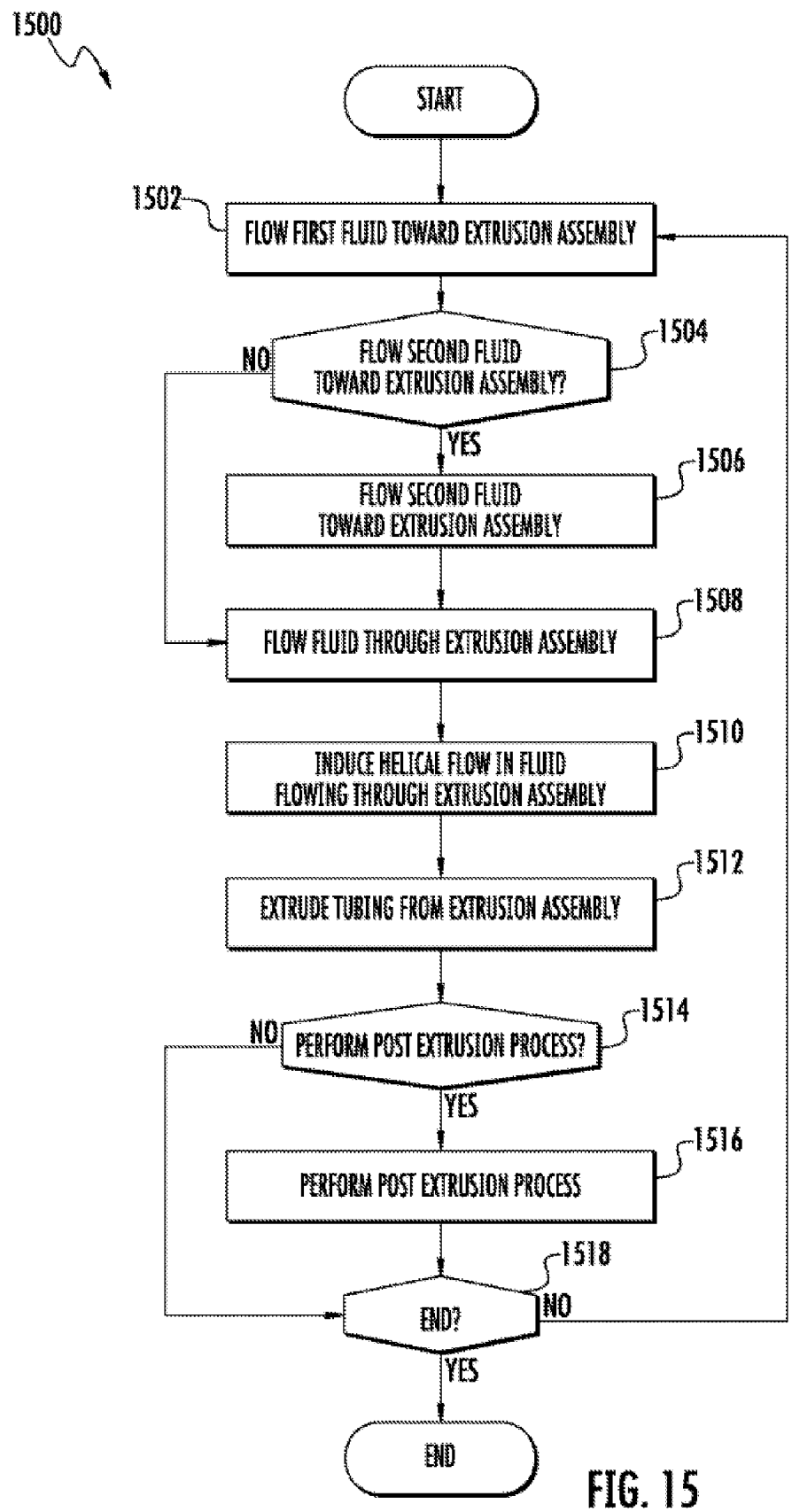
FIG. 15 depicts an example method of producing the examples described herein.

FIG. 15 represents an example method 1500 of producing the examples described herein. At 1502, the method 1500 flows first fluid toward an extrusion assembly. The first fluid may be any suitable polymer, bulk material, bulk extrudate, etc. At 1504, the method 1500 determines whether or not to flow a second fluid toward the extrusion assembly. The second fluid may be any suitable polymer and may have a higher modulus than the first fluid. Enabling the second fluid to flow toward the extrusion assembly enables a co-extruded tube to be produced, for example. If the method 1500 determines to flow the second fluid toward the extrusion assembly, control moves to block 1506.

At 1508, the method 1500 flows fluid through the extrusion assembly. In examples in which the extrusion includes one of the fluids (e.g., the first fluid), the fluid flowing through the extrusion assembly may be the first fluid. In examples in which the extrusion includes two or more fluids (e.g., the first fluid, the second fluid), the fluid flowing through the extrusion assembly may include the first fluid and the second fluid.

In some examples, the first fluid may enter the extrusion assembly at a first location and the second fluid may enter the extrusion assembly at a second location. The first location may be similar or different than the second location. For example, the first location may be at an end of the extrusion assembly and the second location may be at a side of the extrusion assembly.

In some examples, the first fluid may enter the extrusion assembly at a first angle and the second fluid may enter the extrusion assembly at a second angle. The first angle may be similar or different than the second angle. For example, the first fluid may enter the extrusion assembly substantially parallel to and/or along a longitudinal axis of the extrusion assembly and the second fluid may enter the extrusion assembly substantially perpendicular to the longitudinal axis of the extrusion assembly.

At 1510, the method 1500 induces a helical flow in the fluid flowing through the extrusion assembly. The helical flow enables tubing to be produced having helical non-homogeneity characteristics. In some examples, the helical flow may be induced by obstacles (e.g., flow control member) and/or surface structures (e.g., grooves, protrusions, flanges, etc.) of the extrusion assembly. In some examples, the helical flow may be induced by the flow of the second fluid flowing into the extrusion assembly. In some examples, the helical flow may be induced by movement of a portion of the extrusion assembly. For example, the extrusion bushing of the extrusion assembly may rotate and/or the extrusion pin of the extrusion assembly may rotate and/or may be induced to rotate by the fluid flow.

At 1512, the tubing is extruded from the extrusion assembly. At 1514, the method 1500 determines whether or not to perform a post extrusion process(es) on the tubing. If the method 1500 determines to perform a post extrusion process on the tubing, control advances to block 1516. In some examples, the post extrusion process includes cross-linking and/or chemical modification of the tubing to further induce helical non-homogeneity in the tubing. For example, the tubing may be exposed to ionizing radiation, ultraviolet radiation, etc. that moves relative to the tubing being extruded and induces helical geometry in the tubing. In some examples, the post extrusion process includes passing the tubing through a plurality of helical rollers that rotate and/or induce helical non-homogeneity in the tubing being produced.

At 1518, the method determines whether or not to move to block 1502. Otherwise, the example method 1500 is ended.

Figure 16:
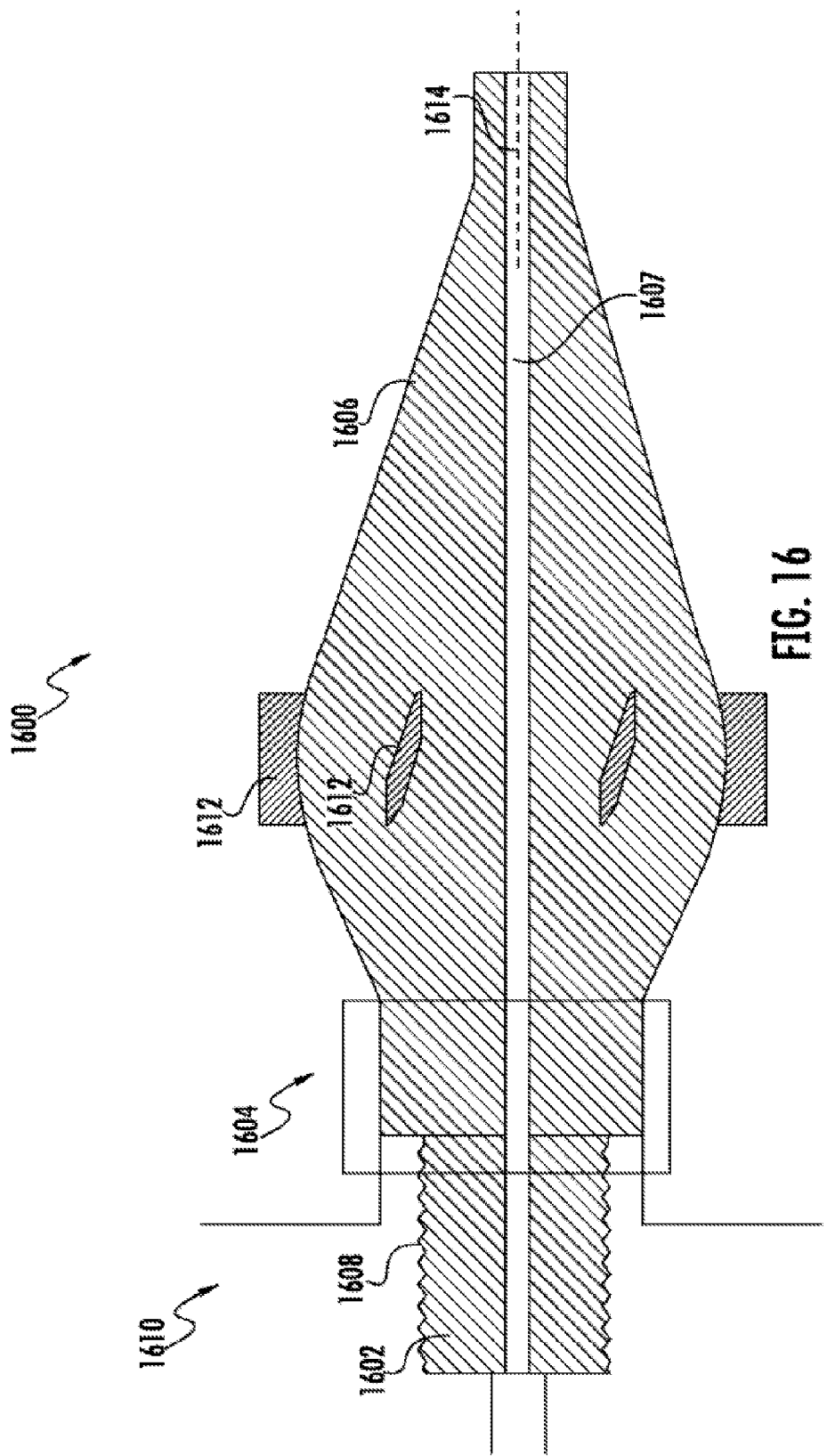
FIG. 16 depicts an example extrusion pin apparatus.
Figure 17:
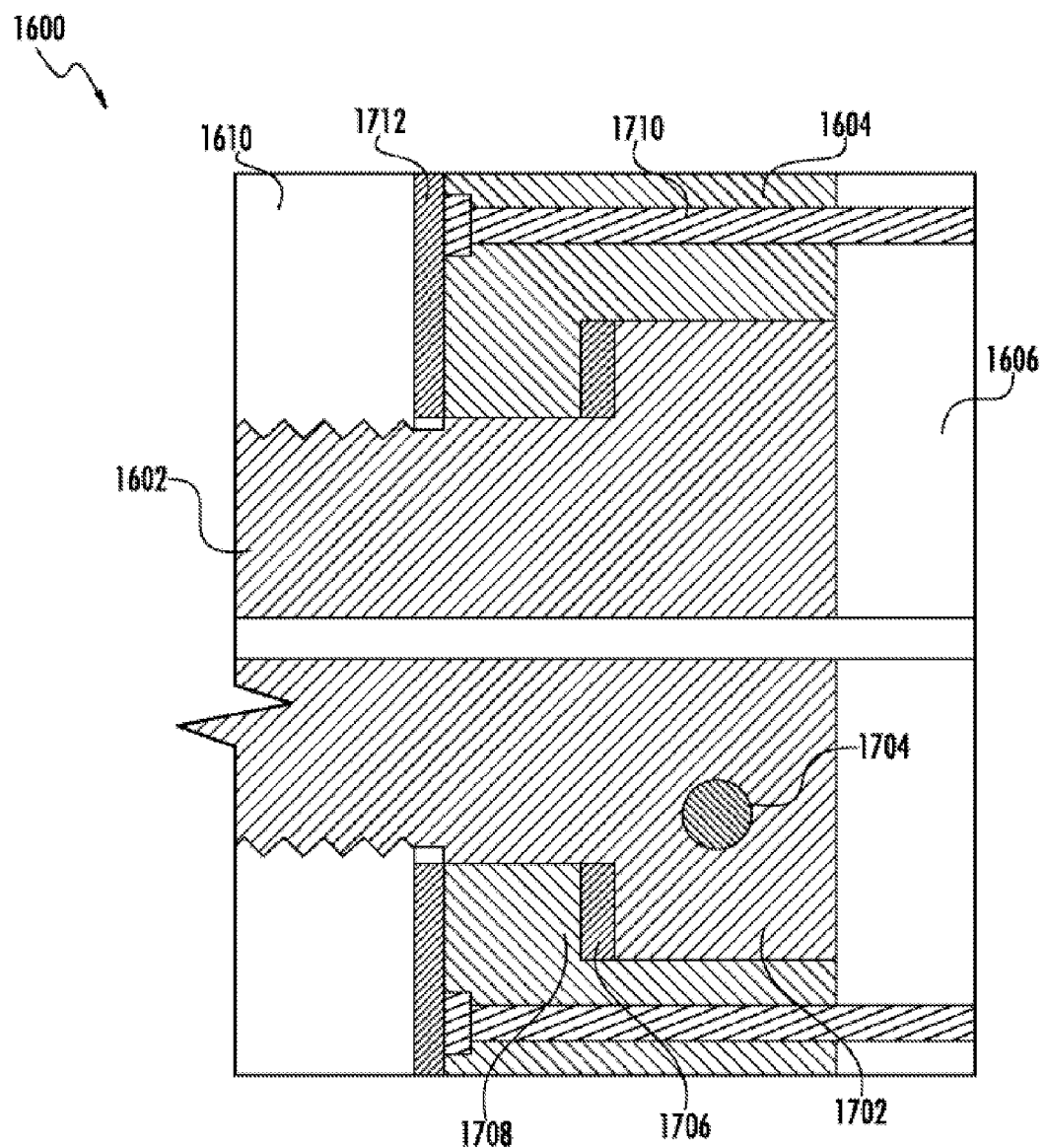
FIG. 17 depicts an enlarged view of a portion of the extrusion pin apparatus shown in FIG. 16.

FIGS. 16 and 17 depict an example extrusion pin or rotating extrusion pin assembly or apparatus 1600 that may be used in connection with an example bushing and/or extrusion assembly to induce a spiral high shear field and, thus, a helical flow in fluid flowing adjacent thereto. The helical fluid flow enables tubes to be extruded having helical non-homogeneity characteristics and being relatively kink resistant, for example.

The example pin 1600 may include a first portion 1602, a second portion or inset 1604 and a third portion or body 1606. The first, second and/or third portions 1602-1606 may define an air passage 1607 therethrough. The first portion 1602 may include threads 1608 to threadably engage a spider 1610, for example. In some examples, the threads 1608 may be in an opposite or different direction than the helical fluid flow to substantially ensure that the fluid flow does not unthread the first portion 1602 from the spider 1610.

The second and third portions 1604 and 1606 may be rotatably coupled to the first portion 1602. In some examples, the third portion 1606 may include a plurality of fins 1612 configured to enable fluid flowing adjacent thereto to rotate the second and third portions 1604 and 1606 and, thus, to induce a helical flow pattern in the fluid. For example, the interaction between the plurality of fins 1612 and the fluid flowing adjacent thereto may provide a driving force to rotate the second and third portions 1604 and 1606 relative to the first portion 1602. The plurality of fins 1612 may be positioned at any suitable angle (e.g., a non-parallel angle, a parallel angle) relative to a longitudinal axis 1614 of the pin 1600. While the example pin 1600 includes 6 fins, any other number of fins (e.g., 1, 2, 3, 4, etc.) may be used that may be spaced (e.g., circumferentially spaced, longitudinally spaced, etc.) on the pin 1600, for example. The plurality of fins 1612 may be sized to enable the third portion 1606 to rotate relative to a bushing surrounding the pin 1600, for example.

Turning to FIG. 17, a detailed view of the first, second and third portions 1602-1606 is depicted. In some examples, the first portion 1602 includes a collar 1702 having a slot or aperture 1704 to receive a tool (e.g., a rod) to facilitate rotating the first portion 1602 relative to the spider 1610. The slot 1704 may enable the first portion 1602 to be relatively easily threaded into the spider 1610, for example. In some examples, once the first portion 1602 is threadably engaged to the spider 1610, a plug (not shown) may be inserted into and/or threaded into the slot 1704 to substantially prevent the slot 1704 from affecting the fluid flow.

In some examples, a first spacer or washer 1706 may be positioned adjacent to the collar 1702. The second portion 1604 may be positioned about the first portion 1602 such that a step 1708 of the second portion 1604 engages the first washer 1706 and is positioned adjacent to the collar 1702. The interaction between the collar 1702, the first washer 1706 and/or the step 1708 enables the second portion 1604 to rotate relative to the first portion 1602, for example. The first and second portions 1602 and 1604 may be coupled to the third portion 1606 by a plurality of fasteners or screws 1710 that threadably engage the third portion 1606, for example.

In some examples, a second washer or spacer 1712 may be positioned about the first portion 1602 and adjacent to the second portion 1604. The first, second and third portions 1602-1606 may be coupled to the spider 1610. In some examples, the second portion 1604 may define an aperture (not shown) that may be aligned with the slot 1704 to enable a rod to be inserted into the slot to facilitate threading the first portion 1602 into the spider 1610 after the first, second and/or third portions 1602-1606 are coupled together. In some examples, the aperture and/or the slot 1704 may define threads orientated in a direction opposite that or different than the fluid to flow adjacent thereto. The orientation of the threads may enable a plug that threadably engages the respective aperture and/or slot 1704 to not become unthreaded by the helical fluid flow, for example. The first and/or second washers 1706 and/or 1712 may be a Teflon washer, a lubricous high temperature washer, etc.

Figure 18:
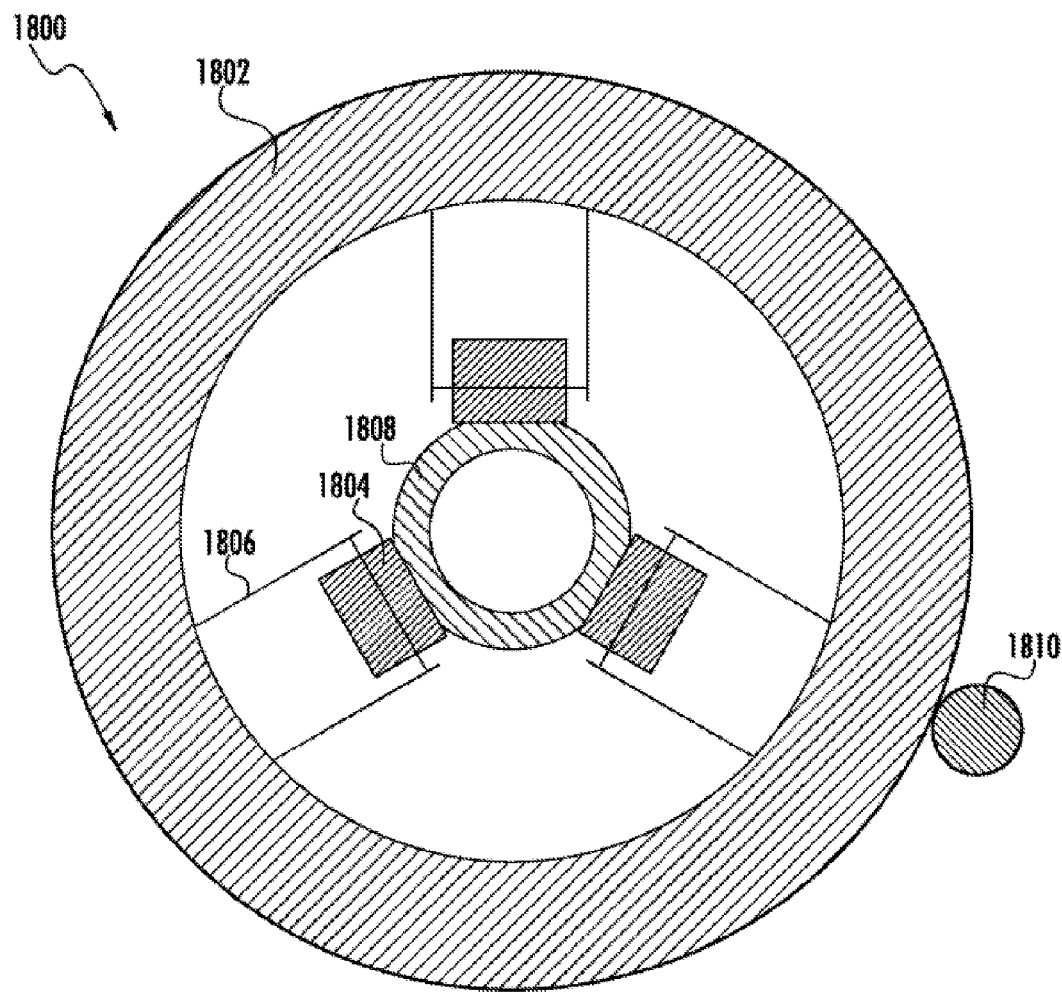
FIG. 18 depicts an example apparatus used to induce a generally helical geometry in tubing.

FIG. 18 depicts an example apparatus 1800 that enables helical orientation to be induced or created in the tubing after exiting the extrusion die using, for example, the example extrusion assemblies described herein. The example apparatus 1800 includes a structure and/or annular ring 1802 and a plurality of rollers 1804 coupled to the annular ring 1802 by fixtures and/or brackets 1806. The plurality of rollers 1804 may be rotatably coupled to the brackets 1806. In some examples, the plurality of rollers 1804 may freely rotate relative to the brackets 1806. In other examples, the plurality of rollers 1804 may be rotated by, for example, a motor (not shown) relative to the brackets 1806.

The plurality of rollers 1804 may have a relatively smooth exterior surface and/or may include a plurality of grooves and/or surface structures, for example. In some examples, some or all of the plurality of rollers 1804 may be positioned to enable the rollers 1804 to rotate in a similar direction (e.g., parallel to) as tubing 1808 being extruded. In some examples, some or all of the plurality of rollers 1804 may be positioned to enable the rollers 1804 to rotate in a different direction (e.g., nonparallel to) as the tubing 1818 being extruded to further induce a helical orientation in the tubing 1808 being produced.

In practice, the ring 1802 may be rotated (e.g., clockwise, counter clockwise) by a drive roller 1810 as the tubing 1808 is being extruded. As the ring 1802 is rotated about the solidified tubing 1808, the plurality of rollers 1804 interact with the molten portion of the tubing 1808 exiting the die, thereby inducing a helical orientation in the tubing 1808, for example. This helical orientation may enable the tubing 1818 produced to be relatively kink resistant. While the example apparatus 1800 includes three rollers 1804, any other number of rollers (e.g., 1, 2, 3, etc.) may be used to induce helical non-homogeneity and/or induce the tubing 1818 to rotate after extrusion, for example. The example apparatus 1800 may be utilized in connection with any of the extrusion assemblies described herein to further induce helical non-homogeneity or may be used on its own to produce tubes having helical non-homogeneity, for example.

Figure 19:
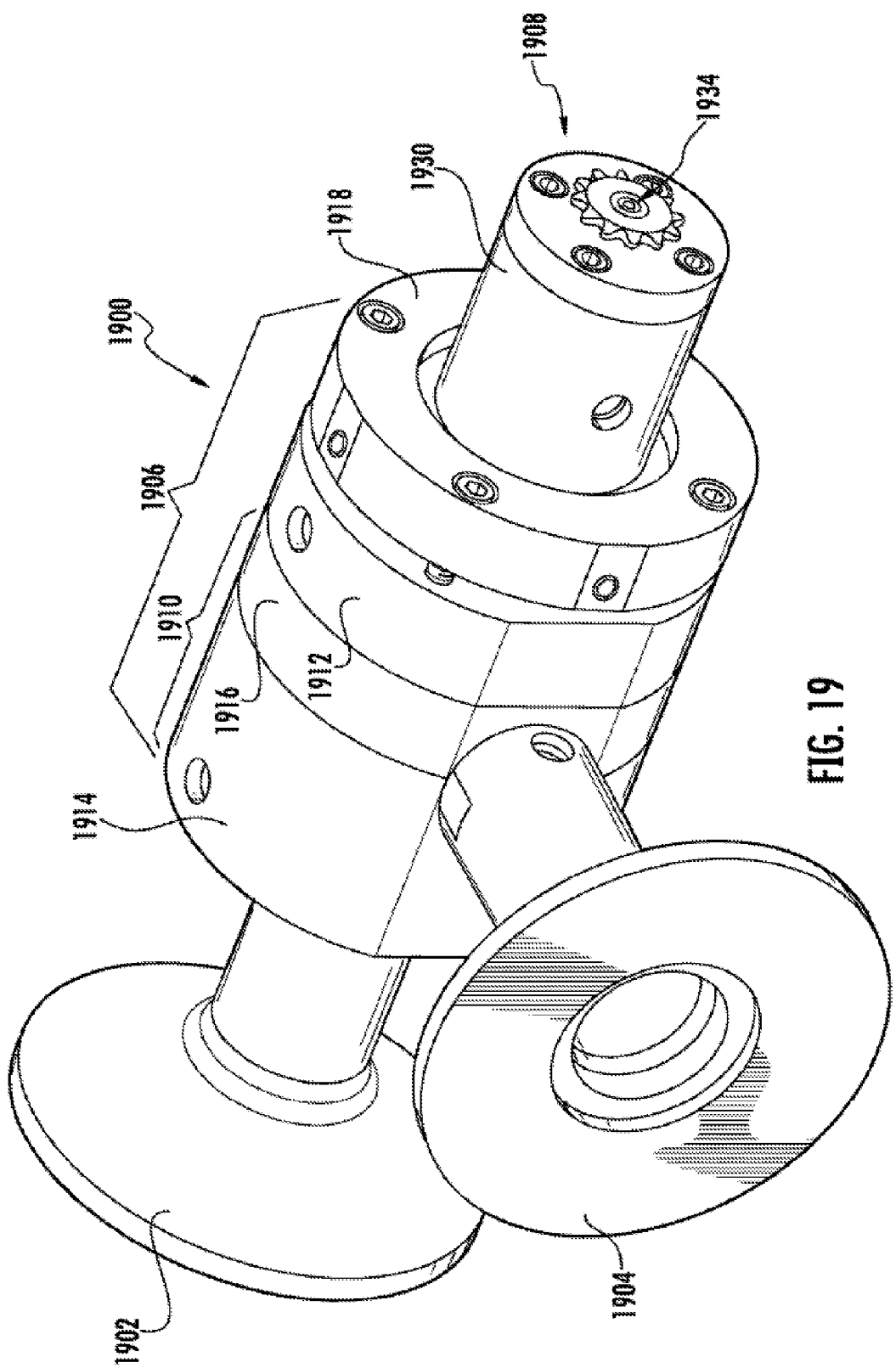
FIG. 19 is a perspective view of an example extrusion die assembly used to produce a flexible tube.

Referring to FIG. 19, an extrusion die assembly 1900 for making a flexible tube is shown according to another example. Die assembly 1900 includes a first inlet structure 1902 and a second inlet structure 1904. Die assembly 1900 includes a die plate assembly 1906 and an extrusion assembly 1908. Die plate assembly 1906 includes a split plate assembly 1910 and a spider plate 1912. In the embodiment shown, split plate assembly 1910 includes a first split plate 1914 and a second split plate 1916. In the example shown in FIG. 19, inlet structure 1902 is coupled to the rear or inlet surface of split plate assembly 1910, and inlet structure 1904 is coupled to the lateral surface of split plate assembly 1910. Spider plate 1912 is coupled to the front surface of split plate assembly 1910. The rear or inlet side of extrusion assembly 1908 is coupled to the front surface of spider plate 1912. A collar 1918 is coupled to the front surface of spider plate 1914 and surrounds the rear or inlet portion of extrusion assembly 1908.

Inlet 1902 and inlet 1904 each include a channel that is in fluid communication with a supply of a polymer material and in fluid communication with polymer flow channels located within die plate assembly 1906 that deliver polymer to extrusion assembly 1908. In one embodiment, inlet 1902 is in communication with a first material that forms the bulk or body of a flexible tube, and inlet 1904 is in communication with a second material that forms helical structure within the flexible tube as shown and discussed below. Thus, as shown, inlet 1902 and 1904 allow for two different materials (e.g., two different polymer materials) to enter the polymer flow path prior to the flow path entering into extrusion assembly 1908.

In one embodiment, the flow path from inlet 1904 within die plate assembly 1906 is split into a plurality of different paths prior to joining with the flow path from inlet 1902. In this embodiment, the flexible tube that is made using die assembly 1900 may have a plurality of helical sections formed of the material from inlet 1904 embedded within a tube body made from the material from inlet 1902.

Figure 20:
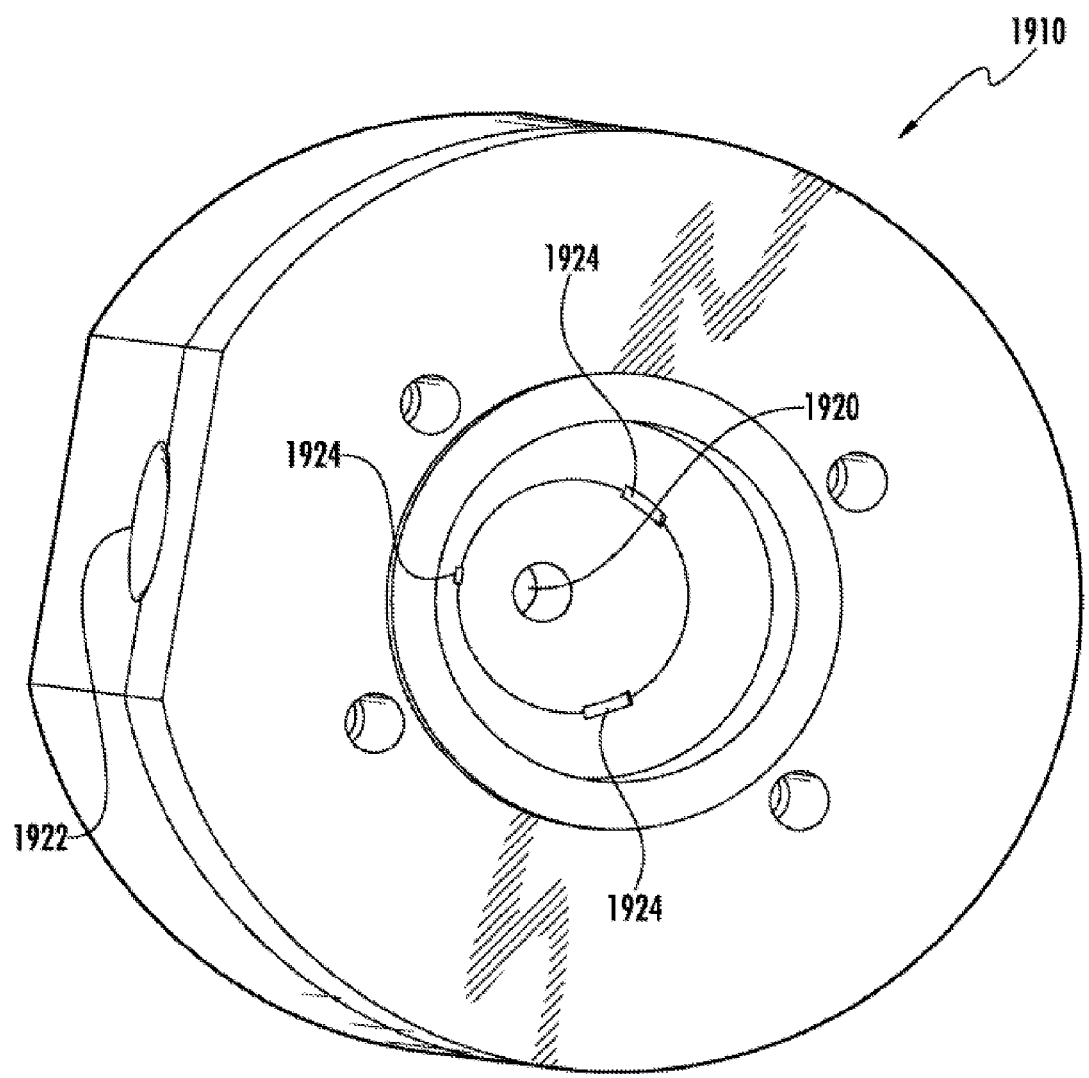
FIG. 20 is a detailed perspective view of the split plate assembly shown in FIG. 19.

In one such embodiment shown in FIG. 20, split plate assembly 1910 includes a rear or inlet channel 1920 that receives polymer fluid flow from inlet 1902 and a side channel 1922 that receives fluid flow from inlet 1904. Side channel 1922 includes three outlet openings 1924 formed through the inner surface of split plate assembly 1910. Outlet openings 1924 are positioned to deposit the second material from inlet 1904 into the flow path of the first material from inlet 1902 at three distinct positions. The arrangement of outlet openings 1924 provides for the formation of a flexible tube having three sections or strips of the material from inlet 1904 embedded in the body of the flexible tube. An example of one such tube is shown below in FIG. 23.

In the embodiment shown in FIG. 20, openings 1924 are evenly spaced (e.g., spaced approximately every 120 degrees) around the internal circumference of split plate assembly 1910 resulting in the even spacing of the strips of the second material within the flexible tube. In other embodiments, split plate assembly may include more than three (e.g., 4, 5, 6, 7, 8, etc.) openings 1924 in order to produce a flexible tubing having more than three strips of the second material. For example, in one example it was found that optimal kink-resistance was achieved for tubing having nine stripes. Openings 1924 may also be spaced non-symmetrically or spaced in other patterns to vary the kink resistant properties of the extruded tube.

Figure 21:
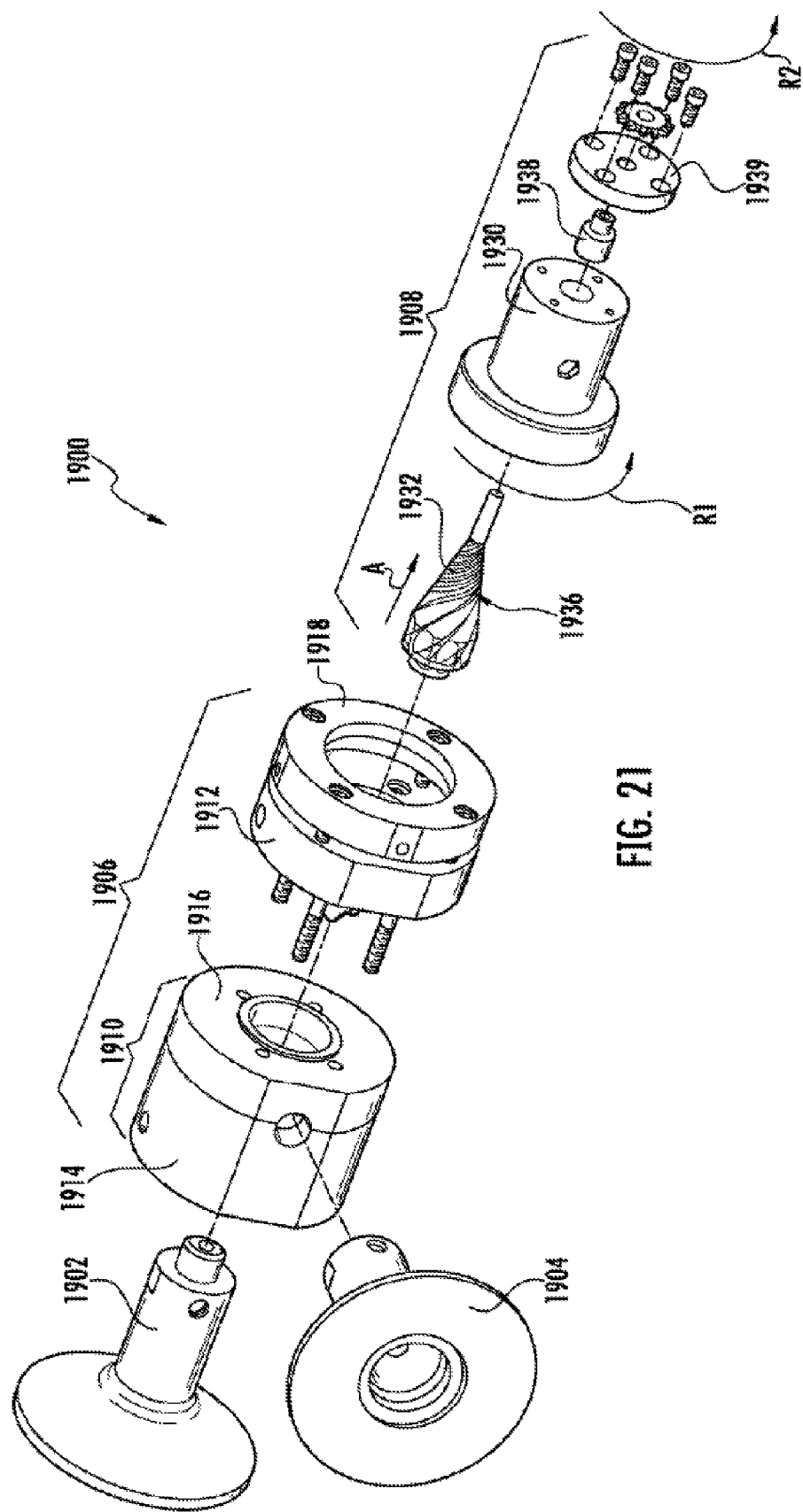
FIG. 21 is an exploded perspective view of an example extrusion assembly used to produce a flexible tube.

Referring to FIG. 19 and FIG. 21, extrusion die assembly 1900 includes an extrusion assembly 1908 coupled to the front face of spider plate 1912. Extrusion assembly 1908 includes a die body, shown as bushing 1930, and an die insert or pin, shown as an extrusion pin 1932. Generally, the die body has an inner surface that defines an internal cavity that receives the die insert, and an extrusion die cavity is defined between the outer surface of the die insert and the inner surface of the die body. With pin 1932 received within the internal cavity, central passage, channel or bore formed through bushing 1930, an extrusion flow channel is defined between the outer surface of pin 1932 and the inner surface of bushing 1930. The extrusion flow channel extends from the rear or inlet side of extrusion assembly 1908 and terminates in an outlet, shown as ring shaped aperture 1934. Ring-shaped aperture 1934 forms a generally tube-shaped article as the flowing polymer exits extrusion assembly 1908 through aperture 1934.

Extrusion assembly 1908 is configured to make or create one or more helically disposed structure or non-homogeneity within the tube by inducing helical rotation (e.g., spiral rotation or non-spiral helical rotation) of the polymer material as it flows through extrusion assembly 1908. Specifically, in the embodiment shown, pin 1932 has a helical groove, shown as spiral groove 1936, formed on the outer surface of pin 1932. Referring to FIG. 21, as polymer flows axially, shown by arrow A, past groove 1936 within the flow channel of extrusion assembly 1908, groove 1936 induces the polymer to rotate in the counterclockwise direction, shown by arrow R1.

In other embodiments, grooves can be oriented in the opposite direction to induce clockwise flow.

Because the external surface of pin 1932 forms the inner surface of the flow channel through extrusion assembly, groove 1936 tends to induce greater rotational flow at the inner surface of the tube (i.e., the surface of the tube that defines the passage or channel through the tube) than at the outer surface of the tube. In one embodiment, the rate of twist of the helical structure (i.e., the number of rotations of the helical structure per unit length of tube) may be greatest at the inner surface of the tube and lowest at the outer surface of the tube. In one such embodiment, the rate of twist of the helical structure is inversely related to its radial position or depth within the wall of the tube and decreases as the radial distance from the lumen of the tube increases.

A portion of bushing 1930 or the entire bushing 1930 may rotate about the extrusion flow path to induce helical rotation in the flowing polymer. Referring to FIG. 21, in one such embodiment, bushing 1930 includes a bushing insert 1938 that is rotatably mounted to the front face of bushing 1930. The inner surface of bushing insert 1938 forms the outer surface of the polymer flow channel through extrusion assembly 1908 and is located adjacent to exit aperture 1934. The front face and front portion of bushing insert 1938 extends through a central hole located in bushing collar 1939, and a sprocket or gear 1940 is coupled to bushing insert 1938. Gear 1940 is coupled to an external power supply (e.g., a motor) that engages and rotates gear 1940 which in turn causes bushing insert 1938 to rotate. The rotation of bushing insert 1938 induces rotation in the polymer material as it flows through bushing insert 1938, which forms one or more helically oriented structures within the tube. As shown, gear 1940 is coaxial with bushing insert 1938 and includes a central aperture that allows the extruded tube to pass through gear 1940. In this embodiment, bushing 1930 is rotationally fixed and bushing insert 1938 rotates relative to bushing 1930. In one embodiment, a bearing may be coupled between bushing insert 1938 and bushing 1930 to facilitate rotation of bushing insert 1938. In another embodiment, bushing 1930 may not include a bushing insert and the whole bushing 1930 may rotate such that the entire outer surface of the extrusion flow channel rotates.

As shown in FIG. 21, bushing insert 1938 is configured to rotate in the counterclockwise direction, as shown by arrow R2. Thus, in the embodiment shown, both groove 1936 and rotating bushing insert 1938 are configured to induce rotation of the polymer in the same direction (e.g., counterclockwise in the embodiment of FIG. 21). In other embodiments, both grooves 1936 and rotating bushing insert 1938 are configured to induce rotation of the polymer in the clockwise direction. In another embodiment, groove 1936 and rotating bushing insert 1938 are configured to induce rotation of the polymer in opposite directions.

Because the internal surface of bushing insert 1938 forms the outer surface of the flow channel adjacent the exit of extrusion assembly 1908, rotation of bushing insert 1938 tends to induce greater rotational flow at the outer surface of the tube than at the inner surface of the tube (i.e., the surface of the tube that defines the passage or channel through the tube). In one embodiment, the rate of twist of the helical structure may be greatest at the outer surface of the tube and lowest at the inner surface of the tube. In one such embodiment, the rate of twist of the helical structure is directly related to the radial position within the wall of the tube and increases as the radial distance from the lumen of the tube increases.

In the embodiment shown in FIG. 21, extrusion assembly 1908 is configured to create rotation of the polymer using both groove 1936 of pin 1932 and via rotation of bushing insert 1938. In this embodiment, rotation of bushing insert 1938 supplements the rotation provided by groove 1936. In one embodiment, the rotational speed of bushing insert 1938 may be set such that the rate of twist of the helical structures at the outer surface and inner surface of the tube are substantially the same. In other embodiments, the rotational speed of bushing insert 1938 may be set such that the rate of twist of the helical structures at the outer surface of the tube is greater than the rate of twist of the helical structures at the inner surface of the tube. In other embodiments, the rotational speed of bushing insert 1938 may be set such that the rate of twist of the helical structures at the outer surface of the tube is greater than the rate of twist of the helical structures at the inner surface of the tube. In other embodiments, the rotational speed of bushing insert 1938 may be set such that the rate of twist of the helical structures at the outer surface of the tube is less than the rate of twist of the helical structures at the inner surface of the tube. In other embodiments, groove 1936 and rotating bushing insert 1938 are configured to induce rotation of the polymer in opposite directions such that the direction of orientation of the helical structures along the inner surface of the tube is opposite from the direction of orientation of the helical structures along the outer surface of the tube.

In some embodiments, a flexible tube is made from a single material using extrusion assembly 1908, and in these embodiments, the rotational flow may induce a helical alignment of polymer chains within the body of the formed tube. In these embodiments, the helical structure embedded in the wall of the tube is the helically aligned polymer chains. In embodiments in which two or more materials are used, the rotation induced by extrusion assembly 1908 creates one or more helically oriented strips or sections of material embedded within the body of the tube instead of or in addition to the helical alignment of polymer molecules.

Figure 22:
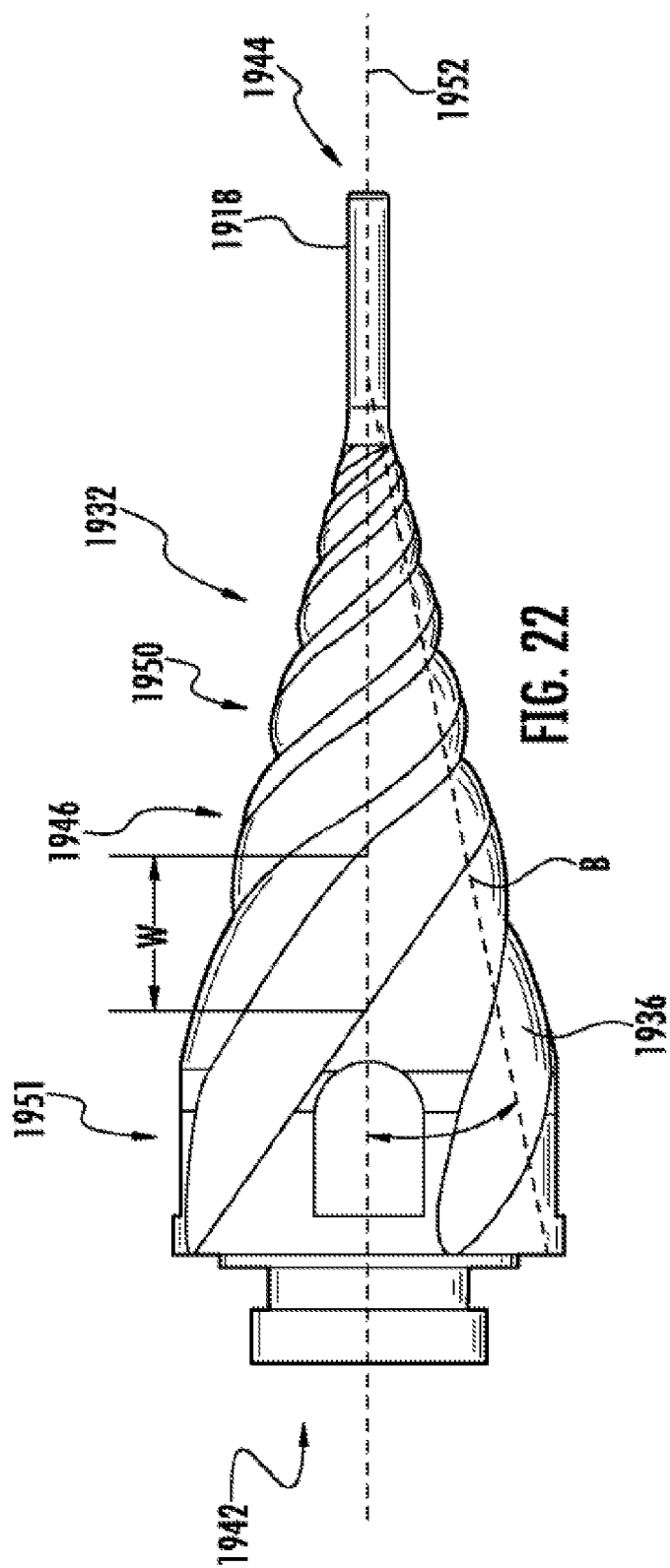
FIG. 22 is a side view of the extrusion pin assembly shown in FIG. 21.

Referring to FIG. 22, a detailed side view of extrusion pin 1932 is shown. Extrusion pin 1932 includes a rear end 1942 and a front end 1944. Extrusion pin 1932 includes a body 1946 and a cylindrical tip portion 1948. Groove 1936 is formed in body 1946 and act to induce rotation of polymer through extrusion assembly 1908 as discussed above. The outer surface of cylindrical tip portion 1948 does not include grooves, and the diameter of tip portion 1948 defines the inner diameter of the tube formed using pin 1932.

As shown in FIG. 22, body 1946 includes a portion 1950 that is angled or tapered such that the diameter of the body decreases as the distance from rear end 1942 increases. Body 1946 also includes a non-tapered, substantially cylindrical portion 1951 located between rear end 1942 and tapered portion 1950. Thus, in this embodiment, the portion of groove 1936 located on tapered portion 1950 is a spiral helical groove, and the portion of groove 1936 located on cylindrical portion 1951 is a non-spiral helical portion. Angle B is the angle between the longitudinal axis 1952 and the lowest or deepest portions of groove 1936 and provides a measurement of the degree of taper along tapered section 1950. In one embodiment, angle B is between about 2 degrees and 30 degrees, specifically between about 5 degrees and 20 degrees, and more specifically between about 10 degrees and 15 degrees. In the embodiment shown in FIG. 22, angle B is about 12 degrees.

As shown in FIG. 22, groove 1936 has a width W which is the dimension of the groove parallel to longitudinal axis 1952. In one embodiment, width W of groove 1936 decreases as the distance from rear end 1942 increases. In other words, the width W of groove 1936 is inversely related (e.g., inversely proportional) to the axial position along pin 1932. Further, width W of groove 1936 decreases as the diameter of pin 1932 decreases. In other words, the width W of groove 1936 at a position along longitudinal axis 1952 is directly related (e.g., directly proportional) to the diameter of pin 1932 at that location. In one embodiment, extrusion pin 1932 having the characteristics discussed above produces a hollow tube having kink resistant properties.

Figure 23:
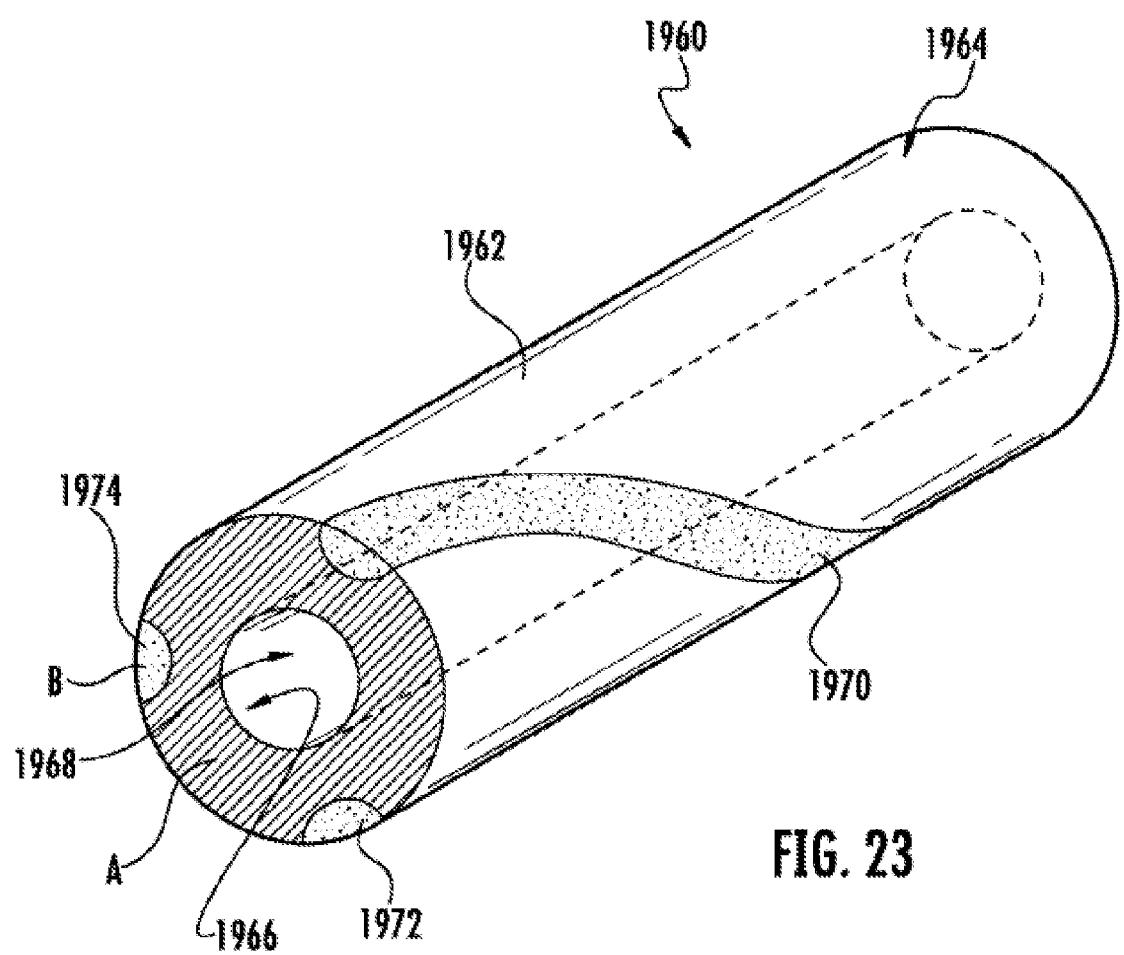
FIG. 23 is a perspective view of an exemplary flexible tube.

FIG. 23 depicts a kink resistant tube, shown as tube 1960, according to an exemplary embodiment. Tube 1960 is an exemplary medical tube that may be produced using the above described apparatuses and methods. Tube 1960 includes a body 1962 having an outer surface 1964 and inner surface 1966. Inner surface 1966 defines a central passage, channel or lumen 1968. In one embodiment, tube 1960 may be a medical tube and lumen 1968 is configured to carry a biological fluid (e.g., blood, urine, etc.), and, in another embodiment, tube 1960 is a medical tube and lumen 1968 is configured to carry a therapeutic fluid (e.g., medicine, drugs, saline, nutrient fluid, etc.). In various embodiments, tube 1960 may be used in conjunction with a medical device or system (e.g., IV bags, pumps, catheters, subcutaneous ports, implanted/implantable medical devices, implanted/implantable drug delivery devices, blood and blood component collection bags, blood collection equipment, blood separation equipment, blood filtration equipment, etc.) to delivery such fluids to a patient or to carry fluids away from a patient.

Tube 1960 includes three or more helical structures, shown as helical segments 1970, 1972 and 1974. Helical segments 1970, 1972 and 1974 are helically disposed along the length of tube 1960 such that the circumferential position of the segment varies with the longitudinal position along tube 1960. In the embodiment of FIG. 23, segments 1970, 1972 and 1974 are evenly spaced around the circumference of tube 1960 such that there is about 120 degrees of separation between adjacent segments.

In the embodiment of FIG. 23, segments 1970, 1972 and 1974 are embedded in body 1962 adjacent outer surface 1964 such that a portion of outer surface 1964 is formed by the outer surfaces of segments 1970, 1972 and 1974. In the embodiment shown, the cross-section of segments 1970, 1972 and 1974 are roughly semi-circular in shape. In other embodiments, as shown in FIG. 6, for example, segments 1970, 1972 and 1974 may be completely embedded within body 1962 such that no portion of segments 1970, 1972 and 1974 is exposed to outer surface 1964.

As shown in FIG. 23, body 1962 of tube 1960 is formed from a first material, shown as material A, and segments 1970, 1972 and 1974 are formed from a second material, shown as material B. In one embodiment, material B is different from the material A. For example, material A may be a first type of polymer (e.g., polyvinylchloride), and material B may be a second type of polymer. In another embodiment, material A may be a material that has a different property (e.g., elasticity, hardness, etc.) than material B. In one such embodiment, material A and material B may be the same general type of polymer but may be species having different material properties. In various embodiments, material A and/or material B may be a nonreactive, biocompatible polymer material.

In one embodiment, both material A and material B may be a PVC material, but material B may be a stiffer, stronger or harder PVC than material A. Specifically, material B may have a durometer greater than the durometer of material A on the Shore A durometer scale. In various embodiments, material A may be PVC material having a Shore A durometer between 60 and 80, and more specifically having a Shore A durometer between 68 and 78. In such embodiments, material B may be a PVC material having a Shore A durometer between 70 and 100 and more specifically between 80 and 90. In one embodiment, material B may be a PVC material having a Shore A durometer of 85.

While PVC may have several advantages and benefits when used to manufacture tubing according to the present disclosure, it should be understood that the present disclosure is not limited to the use of PVC or any other particular materials, as it has been found that many non-PVC materials result in tubing having strong kink resistance. For example, when manufacturing tubing including one or more linear elements, strips, or stripes (e.g., the tubing 1960 of FIG. 23), preferably any two materials having different physical properties (most preferably a difference in modulus, with the higher-modulus material providing the stripe or stripes) may be employed. Exemplary materials include, but are not limited to, an RF-responsive material (e.g., ethylene vinyl acetate or nylon elastomer) for the body of the tubing and polypropylene for the linear element(s), strip(s), or stripe(s).

Figure 24:
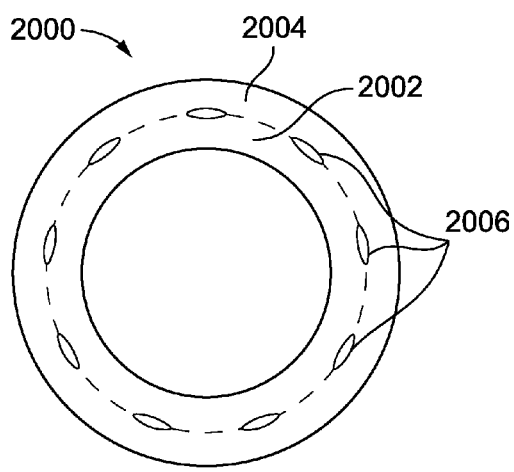
FIG. 24 is a cross-sectional view of a tubing having inner and outer layers and a stripe or segment positioned therebetween.
Figure 24A:
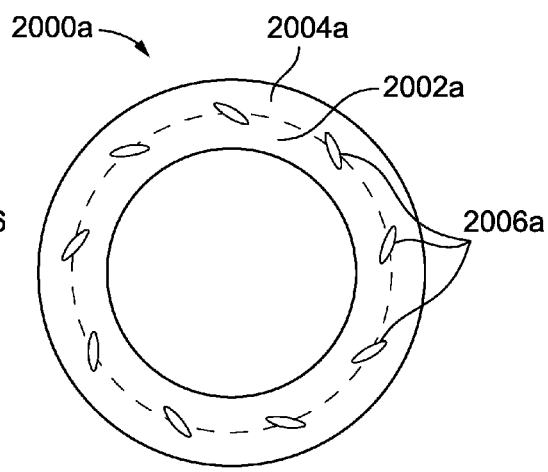
FIG. 24A is a cross-sectional view of another embodiment of a tubing having inner and outer layers and a stripe or segment positioned therebetween.

In addition to the body and stripe(s), a third or outer layer that is coextruded or otherwise applied may be provided to surround the body and stripe(s). FIG. 24 shows an exemplary tubing 2000 employing an inner or body layer 2002, an outer layer 2004 surrounding the inner layer 2002, and a plurality of stripes or segments 2006 embedded between the inner and outer layers 2002 and 2004. FIG. 24A shows an alternative embodiment of the tubing 2000 of FIG. 24, with a tubing 2000a having inner and outer layers 2002a and 2004a, but differing in that the stripes or segments 2006a are applied via one of the helical-flow methods or apparatus described herein, so as to orient them at an angle or non-tangentially with the interface between the inner and outer layers 2002a and 2004a. The outer layer 2004 may be comprised of the same material as the inner layer 2002 or may comprise a third material that imparts desirable surface properties to the tubing 2000. In one embodiment, the outer layer 2004 is comprised of a blend of polypropylene and an elastomer, such as styrene-ethylene/butylene-styrene ("SEBS"), which may allow for cross-linking by radiation (such as shown in FIG. 11 and described above) or chemical means to render the tubing 2000 suitable for sterilization by autoclaving.

Tubing of the type shown in FIGS. 24 and 24A may be manufactured using any one of a number of methods and apparatus. For example, when the inner and outer layers 2002 and 2004 are comprised of the same material, an extrusion apparatus or assembly 2100 (FIG. 25) similar to that of FIGS. 19-21 may be employed. As in the extrusion assembly 1900 of FIGS. 19-21, the extrusion assembly 2100 of FIG. 25 may comprise a first material inlet 2102, a second material inlet 2104 (which may comprise a side inlet), and a die plate assembly 2106 that directs the material to an extrusion die 2108. As in the embodiment of FIGS. 19-21, the die plate assembly 2106 directs the incoming material from the inlets 2102 and 2104 to form the body layer 2002 and the stripes 2006, respectively, as they flow toward the extrusion die 2108. However, the die plate assembly 2106 further includes a flow splitter 2110 positioned within the path of the material entering the die plate assembly 2106 via the first material inlet 2102. The flow splitter 2110 separates the incoming material into two parts, with the first part 2112 being directed to the extrusion die 2108 so as to form the inner layer 2002 and the second part 2114 being directed to the extrusion die 2108 so as to form the outer layer 2004.

Figure 25:
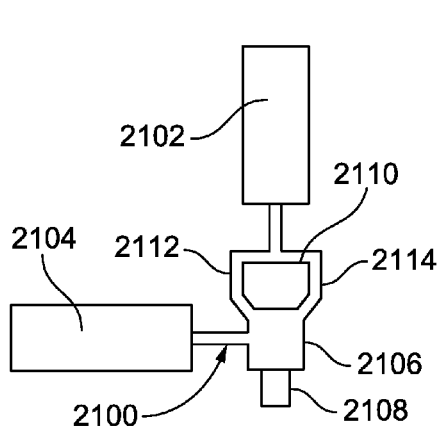
FIG. 25 is a diagrammatic view of an extrusion assembly suitable for manufacturing a tubing of the type shown in FIG. 24.
Figure 26:
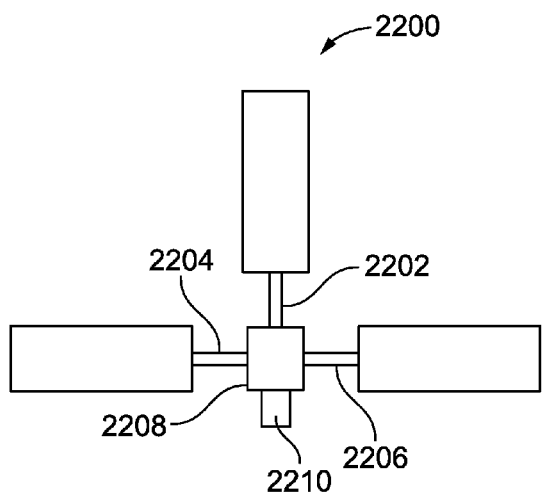
FIG. 26 is a diagrammatic view of an alternative extrusion assembly suitable for manufacturing a tubing of the type shown in FIG. 24.

Alternatively, when the outer layer 2004 is comprised of the same material as the inner layer 2002 or a different material, an extrusion assembly 2200 of the type shown in FIG. 26 may be employed. In the embodiment of FIG. 26, the extrusion assembly 2200 includes three material inlets 2202, 2204, and 2206 in fluid communication with a die plate assembly 2208 which, as in the embodiment of FIG. 25, directs the material from the inlets to an extrusion die 2210. The interior of the die plate assembly 2208 of FIG. 26 may be comparable to that of the die plate assembly 2106 of FIG. 25 to the extent that it directs the inflowing material to the extrusion die 2210 so as to form an inner layer 2002, an outer layer 2004, and one or more stripes or segments 2006. However, rather than employing a flow splitter to separate flow from a single inlet into two parts, the interior of the die plate assembly 2208 of FIG. 26 may be configured to maintain the materials from all three inlets 2202, 2204, and 2206 separate as they flow from their respective inlets into the extrusion die 2210. The material from any one of the inlets may be used to form either layer or the stripes of the tubing 2000 but, in one embodiment, the material entering the die plate assembly 2208 via a first inlet 2202 (which imparts substantially axial flow) may be used to form the inner layer 2002, while the material from a second inlet 2204 (which may be a side inlet) forms the stripes 2006 and material from a third inlet 2206 (which may be a side inlet) forms the outer layer 2004. It should be understood that the extrusion assemblies of FIGS. 25 and 26 are merely exemplary, and other apparatus and methods may be employed in manufacturing tubing of the type shown in FIGS. 24 and 24A.

In addition to the many steps that may be taken during the extrusion process to reduce or prevent kinking, it is also within the scope of the present disclosure to employ post-formation measures (either alone or in combination with the steps taken during the extrusion or formation process) to reduce or prevent kinking. For example, according to one method, after a length of tubing has been formed or extruded (either using one of the methods and/or assemblies described herein or using another method and/or extrusion assembly), it is twisted about its central axis and heated to impart a helical structure therein, which increases kink-resistance.

In one embodiment, one end of the tubing is rotated to a different extent than the other end, which may be achieved by holding one of the ends stationary while the other is rotated about the central axis (either clockwise or counterclockwise) or by rotating the ends in opposite directions about the central axis. Other twisting methods may also be employed without departing from the scope of the present disclosure. For example, both ends of the tubing may be held stationary while the midsection of the tubing is rotated about its central axis at an intermediate point. In yet another embodiment, one end of the tubing may be held stationary while an intermediate point (rather than the other end) of the tubing is rotated about the central axis of the tubing. By rotating the tubing at an intermediate point, the section of the tubing between the intermediate point and the stationary end will become twisted, while the section of the tubing between the intermediate point and the other end remains substantially untwisted. The other end of the tubing may be twisted in the opposite direction or to a different extent in the same direction (while keeping the intermediate point stationary to prevent untwisting or over-twisting) to impart to that section (i.e., the section between the intermediate point and the other end) a different revolutions per distance value (described below) than the aforementioned twisted section between the stationary end and the intermediate point.

A full 360° rotation of one point of the tubing with respect to the another point is referred to herein as a "twist" or "revolution." Hence, when the tubing has been processed such that the ends are 1080° apart from each other (e.g., by rotation one end 1080° while holding the other stationary or rotating one end 900° in one direction and rotating the other end 180° in the other direction, etc.), it can be said that three twists have been imparted to the tubing. Any number of twists or fractions of a twist (e.g., one half twist or 3.75 twists) may be imparted into the tubing after the formation process, although preferably the number of twists is not so many as to cause the tubing to collapse and close. The material composition (including whether there are multiple layers and/or stripes present), length, wall thickness, and intended use of the tubing are some of the factors that may be considered when determining the desired number of twists to impart to the tubing.

An alternative (or companion) value to the total number of twists in a length of tubing is the number of twists or revolutions in a given distance (e.g., revolutions per foot or meter). The desired number of revolutions per distance may vary depending on the same factors as the desired total number of revolutions. In one example, it was found that approximately three revolutions per foot produced the best kink-resistance, but different tubing size or different material may have a different number of optimal revolutions per distance. It is also within the scope of the present disclosure for the revolutions per distance to vary along the length of a given tubing. A varying revolutions per distance value may be imparted by any of a number of methods, such as the twisting method described above in which different sections of the tubing may be twisted in different directions and/or to different degrees.

The twisted tubing is heated and subsequently cooled to impart a helical structure and, hence, kink-resistant properties to it. At least part of the twisting step may be carried out while the tubing is being heated or the two steps may be entirely separate, with the twisting step being completed before the heating step begins. The heating step may be carried out using any suitable means or combination of means, such as an oven or a hot air gun. The duration and temperature (which may vary during the heating process) affect the physical properties of the tubing (including its kink-resistance), so the duration and temperature may vary, depending on the nature and material of the tubing and the use for which it is contemplated. It may be most advantageous to heat the tubing to a temperature approximately equal to the melting point, softening point, or glass transition of the material used to make the tubing. This may include heating the tubing to a temperature equal to, slightly above, or slightly below the melting point, softening point, or glass transition of the material used to make the tubing. In a preferred embodiment, the temperature during the heating step is sufficient to heat the tubing to a temperature below the melting point of the material, but sufficiently high that the tube loses some resiliency and can be deformed without immediately springing back. In one example, plasticized PVC tubing may be heated for at least twenty minutes at a temperature in the range of approximately 210° F. to approximately 280° F. The tendency of the tubing to melt or deform and then recrystallize (once the heating process is ended and the tubing is allowed to cool) is believed to be a factor in imparting a permanent helical structure within the tubing and increasing the kink-resistance of the tubing.

In one embodiment, a tubing is treated to one twisting step, followed by one heating step, but it is also within the scope of the present disclosure for a tubing to be subjected to a number of alternating twisting and heating and cooling steps. Additionally, as noted above, the twisting and heating steps (or at least a portion thereof) may take place simultaneously. Furthermore, the manufacturing process may comprise a batch process (e.g., completely forming and processing a batch of tubing before forming and processing a second batch) or a continuous process (e.g., providing an assembly line on which new tubing may be formed and/or processed while already-formed tubing is being processed).

More than one tubing may be heated at the same time. There are a number of ways to simultaneously process multiple tubings, but FIGS. 27-30 illustrate an exemplary frame 2300 that may be advantageous for such a procedure. The illustrated frame 2300 includes first and second crossbars 2302 and 2304 that extend between first and second supports 2306 and 2308. As will be described in greater detail below, the tubing 2310 is affixed to the crossbars 2302 and 2304, so it may be advantageous for one or both to be adjustably fixed to the supports 2306 and 2308, such that one or both of the crossbars 2302, 2304 may be moved along the supports 2306 and 2308 to modify the distance between the crossbars 2302 and 2304.

In use, at least one tubing 2310 is fixed or secured to one of the crossbars 2302, 2304. FIGS. 27-30 show the ends of the tubing 2310 being secured to the crossbars 2302 and 2304, but it is within the scope of the present disclosure for one or both ends of the tubing 2310 to extend beyond the crossbars 2302 and 2304, with an intermediate point of the tubing 2310 being secured to the crossbar(s) 2302, 2304. This may be advantageous when an end portion of the tubing 2310 is to remain untwisted, which may be achieved by extending that end portion beyond the bounds of the crossbars 2302 and 2304. In the illustrated embodiment, the tubing 2310 is secured to one of the crossbars (the first crossbar 2310 in FIG. 27) by a clamp or fixture 2312, but the tubing may be secured to the crossbars by any suitable means.

With the tubing 2310 secured to one of the crossbars, the portion of the tubing between the crossbars 2302 and 2304 is manipulated to impart to it at least a portion of a twist, as shown in FIG. 28.

When the tubing 2310 has been adequately twisted, it may be secured to the other crossbar (the second crossbar 2304 in FIG. 29) to maintain the twisted configuration. As shown in FIG. 30, a plurality of tubings 2310 may be processed at once using the frame 2300 with either the same or different twisted configurations. Alternatively, rather than securing the tubing 2310 to one of the crossbars before twisting it and securing it to the other crossbar, it is also possible to independently twist the tubing 2310 and then secure it to the two crossbars 2302 and 2304.

While FIG. 29 shows the tubing 2310 secured at only the crossbars 2302 and 2304, it is within the scope of the present disclosure for the tubing 2310 to be secured at other locations. For example, the tubing 2310 may be secured at a location between the crossbars 2302 and 2304, such as by a third clamp or fixture extending from one of the crossbars or supports. This would allow for two sections of the tubing 2310 between the crossbars 2302 and 2304 to have different revolutions per distance values.

When the tubing 2310 has been fully secured to the frame 2300, it may be heated (according to the foregoing description) and then allowed to cool before being removed from the frame 2300.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

For purposes of this disclosure, the term "coupled" means the joining of two components directly or indirectly to one another. Such joining may be stationary in nature or movable in nature. Such joining may be achieved with the two members and any additional intermediate members being integrally formed as a single unitary body with one another or with the two members or the two members and any additional member being attached to one another. Such joining may be permanent in nature or alternatively may be removable or releasable in nature.

The invention claimed is:

1. A method for making a tubing comprising:
    forming a generally tubular inner layer by flowing a first material through an extrusion assembly;
    forming at least one non-tubular segment along the length of the tubing by flowing a second material through the extrusion assembly; and
    forming a generally tubular outer layer coaxial with the inner layer by flowing a third material through the extrusion assembly, wherein said at least one segment is positioned between the inner and outer layers and oriented non-tangentially with an interface between the inner and outer layers.

2. The method of claim 1, wherein said forming a generally tubular inner layer includes inducing a helical rotational flow of the first material flowing through the extrusion assembly.

3. The method of claim 1, wherein said forming at least one non-tubular segment includes forming at least one helical segment.

4. The method of claim 1, wherein said first and third materials are different.

5. The method of claim 4, further comprising introducing the first, second, and third materials into the extrusion assembly using three material inlets.

6. The method of claim 1, wherein said first and third materials are the same.

7. The method of claim 6, further comprising introducing the first and third materials into the extrusion assembly using a single material inlet.

8. The method of claim 7, further comprising providing the extrusion assembly with a flow splitter downstream of the single material inlet and flowing the first and third materials around the flow splitter.

9. The method of claim 1, wherein said forming at least one non-tubular segment includes forming a plurality of non-tubular segments.

10. The method of claim 1, wherein at least one of said materials comprises a non-PVC material.

* * * * *